United States Patent
Nemoto et al.

(10) Patent No.: US 7,887,513 B2
(45) Date of Patent: *Feb. 15, 2011

(54) CHEMICAL LIQUID INJECTION SYSTEM

(75) Inventors: Shigeru Nemoto, Tokyo (JP); Seiichi Ono, Tokyo (JP); Masahiro Sakakibara, Tokyo (JP)

(73) Assignee: Nemoto Kyorindo Co., Ltd, Tokyo (JP)

( * ) Notice: Subject to any disclaimer, the term of this patent is extended or adjusted under 35 U.S.C. 154(b) by 597 days.

This patent is subject to a terminal disclaimer.

(21) Appl. No.: 11/719,089

(22) PCT Filed: Nov. 10, 2005

(86) PCT No.: PCT/JP2005/020607

§ 371 (c)(1), (2), (4) Date: Jan. 21, 2008

(87) PCT Pub. No.: WO2006/051856

PCT Pub. Date: May 18, 2006

(65) Prior Publication Data

US 2008/0125713 A1    May 29, 2008

(30) Foreign Application Priority Data

Nov. 11, 2004  (JP) ............................. 2004-327479

(51) Int. Cl.
*A61M 37/00* (2006.01)

(52) U.S. Cl. ................. 604/154; 604/232; 604/152; 604/151; 604/131; 604/111

(58) Field of Classification Search ............ 604/131, 604/152, 154, 111, 232
See application file for complete search history.

(56) References Cited

U.S. PATENT DOCUMENTS 5,270,717 A  12/1993  Schuermann (Continued)

FOREIGN PATENT DOCUMENTS

EP    1 385 120 A1    1/2004

(Continued)

OTHER PUBLICATIONS

Examiner's comments in the OA dated Jul. 24, 2009 English Translation.

*Primary Examiner*—Nicholas D Lucchesi
*Assistant Examiner*—Leah Stohr
(74) *Attorney, Agent, or Firm*—Knobbe Martens Olson & Bear LLP

(57) ABSTRACT

A chemical liquid injection system which a piston driving mechanism is driven only when a cylinder holding mechanism appropriately holds liquid syringes of various sizes through a cylinder adapter and such manner. When the liquid syringe 200S of a size other than the maximum size is appropriately held by the cylinder holding mechanism 120, RFID chip 230 is located on the side at the rear of metallic cylinder holding mechanism 120. A pair of resonance antennas are disposed on the left and right of the RFID chip, and an RFID reader 131 is disposed below the resonance antennas. When the liquid syringe 200S is appropriately held by the cylinder holding mechanism 120, RFID chip 230 wirelessly communicates with RFID reader 131 favorably, and the piston driving mechanism can be operated only in this state.

84 Claims, 19 Drawing Sheets

U.S. PATENT DOCUMENTS

| | | |
|---|---|---|
| 5,662,612 A | 9/1997 | Niehoff |
| 5,868,710 A | 2/1999 | Battiato et al. |
| 6,019,745 A * | 2/2000 | Gray .......................... 604/131 |
| 6,626,862 B1 * | 9/2003 | Duchon et al. .............. 604/110 |
| 2001/0000430 A1 | 4/2001 | Smith et al. |
| 2003/0233069 A1 | 12/2003 | Gillespie, Jr. et al. |
| 2004/0051368 A1 | 3/2004 | Caputo et al. |

FOREIGN PATENT DOCUMENTS

| | | |
|---|---|---|
| JP | 2003-218624 A | 7/2003 |
| JP | 2004-243009 | 2/2004 |
| WO | PCT/GB94/00909 | 11/1994 |
| WO | WO 97/49076 A | 12/1997 |
| WO | PCT/DK02/00111 | 8/2002 |

* cited by examiner (a)

(b)

CHEMICAL LIQUID INJECTION SYSTEM

CROSS REFERENCE TO RELATED APPLICATIONS

This application claims to benefit and priority to and is a U.S. National Phase of PCT International Application Number PCT/JP2005/20607, filed on Nov. 10, 2005, designating the United States of America, which claims priority under U.S.C. §119 to Japanese Application 2004-327479 filed on Nov. 11, 2004. The disclosures of the above-referenced applications are hereby incorporated by this reference in their entirety.

TECHNICAL FIELD

The present invention relates to a chemical liquid injection system for injecting a liquid in a liquid syringe into a patient by a chemical liquid injector, and more particularly, to a chemical liquid injection system for injecting a contrast medium into a patient whose diagnostic images are taken by an diagnostic imaging apparatus such as a CT (Computed Tomography) scanner.

BACKGROUND ART

Presently available diagnostic imaging apparatuses for capturing diagnostic images of patients include CT scanners, MRI (Magnetic Resonance Imaging) apparatuses, PET (Positron Emission Tomography) apparatuses, ultrasonic diagnostic apparatuses, CT angiography apparatuses, MRA (MR angiography) apparatuses and the like. When the abovementioned diagnostic imaging apparatuses are used, a liquid such as a contrast medium and physiological saline may be injected into a patient. Chemical liquid injectors for automatically performing the injection have been put into practical use.

Such a chemical liquid injector has a piston driving mechanism having a driving motor, a slider mechanism and the like, for example. A liquid syringe is removably mounted on the injector. The liquid syringe typically includes a cylinder member and a piston member slidably inserted in the cylinder member.

More specifically, the cylinder member is formed in a cylindrical shape, and has an opened trailing end and a closed leading end having a conduit formed at the center thereof. An annular cylinder flange is formed in the outer circumference of the trailing end of the cylinder member, and the piston member is slidably inserted into the cylinder member through the opening at the trailing end. The piston member is formed in a cylindrical shape and has an annular piston flange formed in the outer circumference of a trailing end.

There are a pre-filled type and a refill type in the liquid syringe. The liquid syringe of the pre-filled type includes a cylinder member filled with a liquid and is wholly sealed by a packing material for shipment. The liquid syringe of the refill type includes a cylinder member which can be filled with a desired liquid by a user. For simplicity, the following description will be made assuming that the liquid syringe of the pre-filled type is used.

When the liquid in the liquid syringe of the abovementioned type is injected into a patient, an operator prepares a liquid syringe containing an appropriate liquid and takes out the liquid syringe from the packing material. The operator connects the liquid syringe to a patient through an extension tube and mounts the liquid syringe on a chemical liquid injector. The cylinder flange is held by a cylinder holding mechanism. In this state, the chemical liquid injector presses the piston member into the cylinder member with a piston driving mechanism in accordance with a predetermined operation to inject the liquid into the patient from the liquid syringe.

The operator determines the rate at which the liquid is injected and the total quantity of the liquid to be injected in view of the type of the liquid and the like, and enters data representing the rate and total quantity into the chemical liquid injector. The chemical liquid injector injects the liquid into the patient based on the entered data. For example, if a contrast medium is injected as the liquid, the image contrast of the patient is changed to allow the diagnostic imaging apparatus to capture a favorable diagnostic image of the patient.

Some chemical liquid injectors can inject physiological saline as well as the contrast medium into the patient. In such a chemical liquid injector, the operator enters as desired an instruction to inject the physiological saline following the completion of the injection of the contrast medium, together with data representing the injection rate and total quantity of the physiological saline, into the chemical liquid injector. Based on the entered data, the chemical liquid injector first injects the contrast medium into the patient and then automatically injects the physiological saline. The subsequently injected physiological saline can push the previously injected contrast medium to reduce the consumption of the contrast medium and also can reduce artifacts in the captured image.

The contrast medium has a high viscosity, but the chemical liquid injector can insert the piston member into the cylinder member of the liquid syringe at high pressure and is preferably used for injection of the contrast medium. To insert the piston member into the cylinder member at high pressure, the cylinder member needs to be held securely.

Thus, a chemical liquid injector applied for patent by the applicant of the present application includes a pair of metallic flange holding members supported openably and closeably to hold individually the left and the right of a cylinder flange of a liquid syringe inserted from above (see, for example, non-patent document 1 below).

Non-patent document 1: "Dual Shot/A-300 in product guides of Nemoto Kyorindo Co., Ltd" (retrieved in Jun. 30, 2004) (URL:http://www.nemoto-do.co.jp/seihin_ct.html#dual)

DISCLOSURE OF THE INVENTION

Subject to be Solved by the Invention

In the chemical liquid injectors as described above, the pair of metallic flange holding members can securely hold the cylinder flange of the liquid syringe, so that the piston member can be inserted into the cylinder member of the liquid syringe at high pressure to satisfactorily inject the contrast medium with high viscosity and the like into a patient.

In typical liquid syringes currently used, the cylinder flange has a pair of flat portions in parallel at opposite positions on the annular outer circumference in order to prevent unnecessary rolling and the like of the liquid syringe. The abovementioned chemical liquid injector is formed to hold the annular portion of the cylinder flange with the flange holding members, and the operator needs to ensure the holding of the annular portion of the cylinder flange with the flange holding members without fail.

If the flange holding members hold the flat portions of the cylinder flange, however, the operator may see it as if the liquid syringe was appropriately held in the chemical liquid injector. In this case, since the flange holding members hold the cylinder flange with a smaller area, the cylinder flange may be broken.

In the abovementioned chemical liquid injector, when the liquid in the liquid syringe is injected into the patient, the operator needs to select the appropriate liquid syringe in order to inject the appropriate liquid. However, some liquid syringes have the same or similar appearances even when they contain different types of liquid, which leads to the possibility that the operator mounts the liquid syringe containing an inappropriate liquid on the chemical liquid injector.

In some cases, an improper product may be used as a liquid syringe, and their inappropriate performance such as low resistance to pressure may cause medical malpractice. The liquid syringe of the pre-filled type should be discarded after it is used once in order to prevent infection and the like. As for the currently available chemical liquid injectors, however, it is impossible to prevent reuse of a liquid syringe after it is used once.

As described above, the operator needs to enter data representing the injection rate and total quantity of the liquid and the like for each of the liquid and the liquid syringe into the chemical liquid injector. Since the entry operation is complicated and difficult for an unskilled operator, entry of incorrect numerical values cannot be avoided. The currently available contrast media contain active ingredients which differ in concentration several fold at maximum. If correct numerical values are not entered, the patient may be injected with the contrast medium of the quantity which is several times larger than or a fraction of the appropriate quantity.

The operator needs to enter data representing the injection rate or the like of the liquid into the chemical liquid injector in some cases based on the area to be imaged and the weight of the patient. The operation is also complicated and erroneous entry cannot be prevented. The present applicant has applied Japanese patent application No. 2002-281109 in which a contrast medium is injected at a variable rate to improve the resulting image contrast, but it is not easy to specify the data representing such a variable pattern in the chemical liquid injector.

To solve the abovementioned problems, the present applicant has applied Japanese patent application No. 2003-098058 in which various types of data are recorded on the packing material of a liquid syringe or the like, for example with a bar code, and the bar code is read by the chemical liquid injector to retrieve the recorded data. However, the bar code has a small data capacity, so that only limited data such as identification data can be recorded.

Thus, in the abovementioned chemical liquid injector, a large amount of various types of data such as the variable pattern is previously registered and then retrieved according to the reading of the bar code. However, this requires the previous recording of the various types of data in the chemical liquid injector, and when the recorded data needs to be renewed, the data needs to be updated in the chemical liquid injector.

The present invention has been made in view of the abovementioned problems, and it is an object thereof to provide a chemical liquid injection system which can automatically prevent driving of a piston driving mechanism while a liquid syringe is not appropriately held by a cylinder holding mechanism.

Means to Solve the Subject

According to a first aspect and a fourth aspect of the present invention, a chemical liquid injection system includes a liquid syringe and a chemical liquid injector. The chemical liquid injector includes a cylinder holding mechanism, a piston driving mechanism, an RFID reader, a resonance antenna, and an operation control means. The liquid syringe includes a cylinder member and a piston member, and the piston member is slidably inserted from behind into the cylinder member formed in a cylindrical shape and having an annular cylinder flange formed in the outer circumference of the trailing end. The cylinder holding mechanism of the chemical liquid injector individually holds the left and right of the cylinder flange of the liquid syringe inserted from above. The piston driving mechanism at least inserts the piston member into the held cylinder member with pressure.

An RFID chip for wirelessly transmitting recorded data is placed at a predetermined position on the cylinder member of the liquid syringe. The RFID chip includes a chip antenna in a predetermined plane shape or elongated shape connected to a circuit chip. The RFID chip is put on the outer circumference of the cylinder member of the liquid syringe such that substantially the center of the RFID chip is located on the left or right of the cylinder member when the liquid syringe is held by the cylinder holding mechanism in a particular orientation in rotation about the axis.

The RFID reader of the chemical liquid injector includes a reader antenna in a predetermined plane shape or elongated shape connected to a communication circuit to wirelessly receive recorded data from the RFID chip. The operation control means allows the operation of the piston driving mechanism only when the recorded is wirelessly received. The chemical liquid injector includes the reader antenna disposed in a plane or longitudinal direction substantially in parallel with the chip antenna and on one of the left and right of the piston member and the resonance antenna in a predetermined plane shape disposed on the other of the left and right in the state in which the cylinder member is held by the cylinder holding mechanism in the particular orientation.

Thus, in the chemical liquid injection system of the present invention, in the state in which the liquid syringe is held in the particular orientation by the cylinder holding mechanism, the chip antenna, the reader antenna, and the resonance antenna are substantially in parallel with each other, and these antennas favorably resonate a radio signal. The data recorded on the RFID chip is wirelessly received by the RFID reader, so that the piston driving mechanism enters the state in which it can insert the piston member into the cylinder member with pressure.

In the state in which the liquid syringe is held by the cylinder holding mechanism at an angle rotated from the particular orientation, however, the chip antenna is not substantially in parallel with the reader antenna or the resonance antenna, and these antennas do not resonate a radio signal favorably. The data recorded on the RFID chip is not received wirelessly by the RFID reader, so that the piston driving mechanism does not enter the state in which it can insert the piston member into the cylinder member with pressure.

According to a second aspect and a fifth aspect of the present invention, a chemical liquid injection system includes a chemical liquid injector including a pair of resonance antennas and an interfering conductor. In the chemical liquid injector, a reader antenna is placed below a piston member in a direction substantially orthogonal to a chip antenna when a cylinder holding mechanism holds a cylinder member in a particular orientation.

In the chemical liquid injector, the paired resonance antennas are placed on the left and right of the piston member in a direction substantially parallel with the chip antenna when the cylinder holding mechanism holds the cylinder member in a particular orientation. The interfering conductor is placed immediately below an RFID chip in a direction substantially parallel with the chip antenna when the cylinder holding mechanism holds the cylinder member in an orientation orthogonal to the particular orientation.

Thus, in the chemical liquid injection system of the present invention, in the state in which the liquid syringe is held by the cylinder holding mechanism in the particular orientation, the chip antenna is substantially in parallel with the paired resonance antennas, and these antennas favorably resonates a radio signal. The resonance amplifies the radio signal between the RFID chip and the RFID reader, so that the data recorded on the RFID chip is wirelessly received by the RFID reader, and the piston driving mechanism enters the state in which it can insert the piston member into the cylinder member with pressure.

In the state in which the liquid syringe is held by the cylinder holding mechanism at an angle rotated from the particular orientation, however, the chip antenna is not substantially in parallel with the paired resonance antennas, and these antennas do not resonate a radio signal favorably. The radio signal between the RFID chip and the RFID reader is not amplified, and the data recorded on the RFID chip is not received wirelessly by the RFID reader, so that the piston driving mechanism does not enter the state in which it can insert the piston member into the cylinder member with pressure.

In the state in which the liquid syringe is held by the cylinder holding mechanism at an angle where the circuit chip of the RFID chip is located below, the RFID chip is close to the RFID reader, but the interfering conductor intervenes between them. Since this prevents the data recorded on the RIFD chip from being received wirelessly by the RFID reader, the piston driving mechanism does not enter the state in which it can insert the piston member into the cylinder member with pressure.

According to a third aspect and a sixth aspect of the present invention, a chemical liquid injection system includes liquid syringes of various sizes and cylinder adapters associated with the liquid syringes of sizes other than the maximum size. In a chemical liquid injector, the liquid syringe of the maximum size is directly mounted, and a liquid syringe of a size other than the maximum size is mounted with a cylinder adapter used between them.

The cylinder adapter is made of a material which does not prevent wireless communication and individually holds the left and right of a cylinder flange of the liquid syringe inserted from above. A cylinder holding mechanism of the chemical liquid injector individually holds the left and right of the cylinder flange of the liquid syringe of the maximum size inserted from above with a pair of metallic flange holding members and holds the cylinder adapter inserted from above.

An RFID chip is put on the liquid syringe of the maximum size such that substantially the center of the RFID chip is located at the top or bottom of the cylinder member when the liquid syringe is held by the cylinder holding mechanism in a particular orientation in rotation about the axis. An RFID chip is put on the liquid syringe of the size other than the maximum size such that substantially the center of the RFID chip is located on the left and right of the cylinder member in the state in which the liquid syringe is held by the cylinder adapter put in the cylinder holding mechanism in the particular orientation.

In the chemical liquid injector, a reader antenna is placed below a piston member in a direction substantially in parallel with a chip antenna when the cylinder holding mechanism holds the liquid syringe of the maximum size in the particular orientation. The paired resonance antennas are placed substantially in parallel on the left and right of the piston member in a direction substantially orthogonal to the chip antenna when the cylinder holding mechanism holds the liquid syringe of the maximum size in the particular direction.

In the chemical liquid injector, an auxiliary antenna is placed immediately below the RFID chip in a direction substantially in parallel with the chip antenna when the cylinder holding mechanism holds the liquid syringe of the maximum size in the particular orientation. In the cylinder adapter, the interfering conductor longer and larger than the reader antenna is placed at the position overlapping the auxiliary antenna in the state in which the cylinder adapter is held by the cylinder holding mechanism.

In the state in which the liquid syringe of the size other than the maximum size is held by the cylinder adapter put in the cylinder holding mechanism, the chip antenna is located at the rear of the flange holding members.

Thus, in the chemical liquid injection system of the present invention, in the state in which the liquid syringe of the maximum size is held by the cylinder holding mechanism in the particular orientation, the chip antenna, the auxiliary antenna, and the reader antenna are substantially in parallel, so that the data recorded on the RFID reader is wirelessly received by he RFID reader via the auxiliary antenna. The piston driving mechanism enters the state in which it can insert the piston member into the cylinder member with pressure.

In the state in which the liquid syringe of the maximum size is held by the cylinder holding mechanism at an angle rotated from the particular orientation, however, the chip antenna is not substantially in parallel with the auxiliary antenna and the reader antenna, so that the data recorded on the RFID chip is not received wirelessly by the RFID reader, and the piston driving mechanism does not enter the state in which it can insert the piston member into the cylinder member with pressure.

In the state in which the liquid syringe of the maximum size is held by the cylinder holding mechanism at an angle rotated substantially right angle from the particular orientation, the chip antenna is substantially in parallel with the paired resonance antennas, but the metallic flange holding members intervene between them. This prevents the data recorded on the RFID chip from being received wirelessly by the RFID reader, so that the piston driving mechanism does not enter the state in which it can insert the piston member into the cylinder member with pressure.

On the other hand, in the state in which the liquid syringe of the size other than the maximum size is held in the particular direction by the cylinder adapter put in the cylinder holding mechanism, the chip antenna located at the rear of the flange holding members is substantially in parallel with the paired resonance antennas, so that these antennas favorably resonate a radio signal. Since the resonance amplifies the radio signal between the RFID chip and the RFID reader, the data recorded on the RFID chip is wirelessly received by the RFID reader, and the piston driving mechanism enters the state in which it can insert the piston member into the cylinder member with pressure.

In the state in which the liquid syringe of the size other the maximum size is held by the cylinder adapter put in the cylinder holding mechanism at an angle rotated from the particular orientation, however, the chip antenna is not substantially in parallel with the paired resonance antennas, and these antennas do not resonate a radio signal favorably. The radio signal between the RFID chip and the RFID reader is not amplified, and the data recorded on the RFID chip is not received wirelessly by the RFID reader, so that the piston driving mechanism does not enter the state in which it can insert the piston member into the cylinder member with pressure.

In the state in which the liquid syringe of the size other than the maximum size is held by the cylinder holding mechanism at an angle where the circuit chip of the RFID chip is located below, the RFID chip is close to the RFID reader, but the interfering conductor intervenes between them. Since this prevents the data recorded on the RIFD chip from being received wirelessly by the RFID reader, the piston driving mechanism does not enter the state in which it can insert the piston member into the cylinder member with pressure.

Various means referred to in the present invention may be arranged to perform their functions, and may comprise dedicated hardware for performing a predetermined function, a data processing apparatus whose predetermined function is given by a computer program, a predetermined function performed in a data processing apparatus according to a computer program, or a combination thereof.

Various components referred to in the present invention do not need to be separate entities. A plurality of components may be constructed as one member, a single component may be constructed by a plurality of members, a certain component may be part of another component, or a certain component may have a portion overlapping a portion of another component.

Although the directions of forward, rearward, left, right, up, and down are specified as shown in the description of the present invention, these directions are defined for convenience to simply describe the relative relationship between components of the present invention and the definition does not limit any direction in manufacture or actual use when the present invention is implemented.

Effect of the Invention

In the chemical liquid injection system of the present invention, the recorded data on the RFID chip can be wirelessly received by the RFID reader only when the liquid syringe is appropriately held by the cylinder holding mechanism, so that the piston driving mechanism enters the state in which it can insert the piston member into the cylinder member. It is thus possible to automatically prevent insertion of the piston member into the cylinder member in the state in which the liquid syringe is not appropriately held.

DESCRIPTION OF REFERENCE NUMERALS

Figure 1:
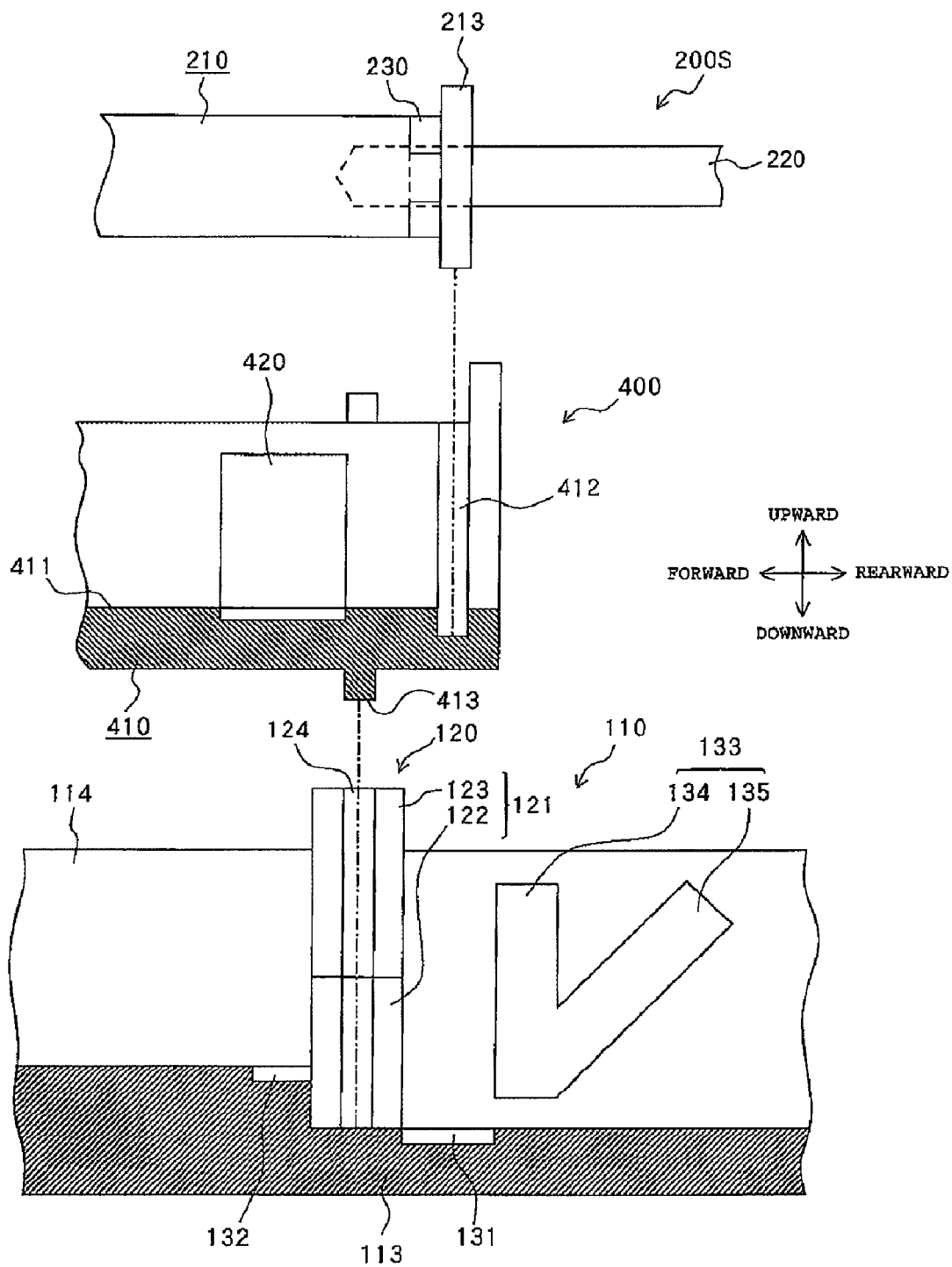
FIG. 1 is a longitudinal section view schematically showing how to mount a chemical liquid syringe on a chemical liquid injector which is an embodiment of the present invention.

100 CHEMICAL LIQUID INJECTOR
116 PISTON DRIVING MECHANISM
120 CYLINDER HOLDING MECHANISM
120 CYLINDER HOLDING MECHANISM
121 FLANGE HOLDING MEMBER
130 RFID READER
131 READER ANTENNA
132 AUXILIARY ANTENNA
133 RESONANCE ANTENNA
134 BODY PART
135 INCLINED PORTION
140 COMPUTER UNIT serving as various means
150 Operation Control Means
151 CHECK STORING MEANS
152 DATA COMPARING MEANS
153 ALARM OUTPUTTING MEANS
154 DATA ACCUMULATING MEANS
156 DATA HOLDING MEANS
157 DISPLAY CONTROL MEANS
158 INJECTION CONTROL MEANS
200 CHEMICAL LIQUID SYRINGE
210 CYLINDER MEMBER
213 CYLINDER FLANGE
230 RFID CHIP
232 CIRCUIT CHIP
233 CHIP ANTENNA
300 CT SCANNER serving as diagnostic imaging apparatus
400 CYLINDER ADAPTER
420 INTERFERING CONDUCTOR
1000 CHEMICAL LIQUID INJECTION SYSTEM

BEST MODE FOR CARRYING THE INVENTION

Configuration of Embodiment

An embodiment of the present invention will hereinafter be described with reference to the drawings. As shown in FIGS. 9 to 12, chemical liquid injection system 1000 of the embodiment according to the present invention comprises chemical liquid injector 100, liquid syringe 200, CT scanner 300 which is a diagnostic imaging apparatus, and cylinder adapter 400. The system is provided for taking diagnostic images of a patient (not shown) injected with a liquid such as a contrast medium, described later in detail.

Figure 11:
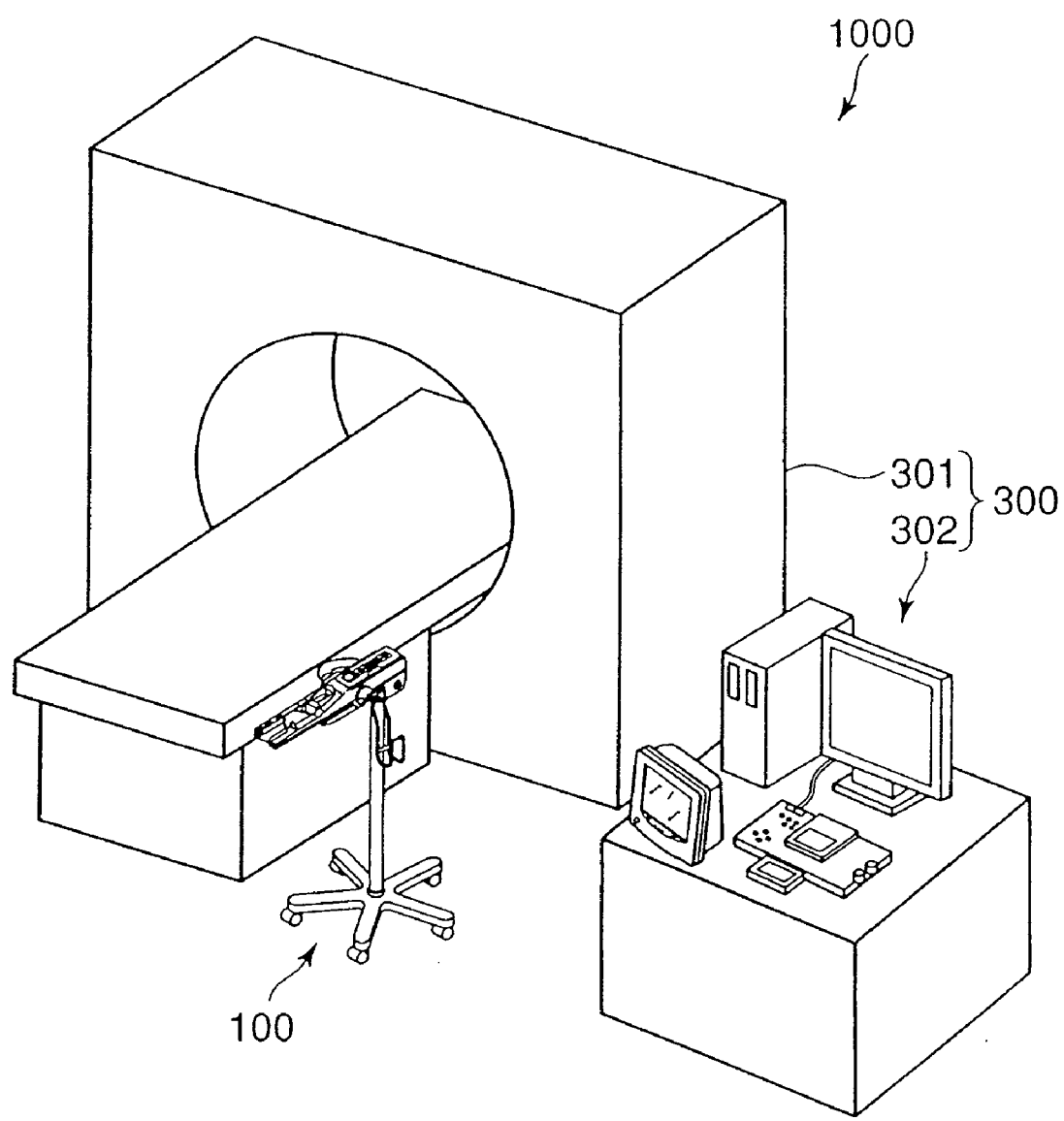
FIG. 11 is a perspective view showing the outer appearance of a CT scanner serving as a diagnostic imaging apparatus.
Figure 12:
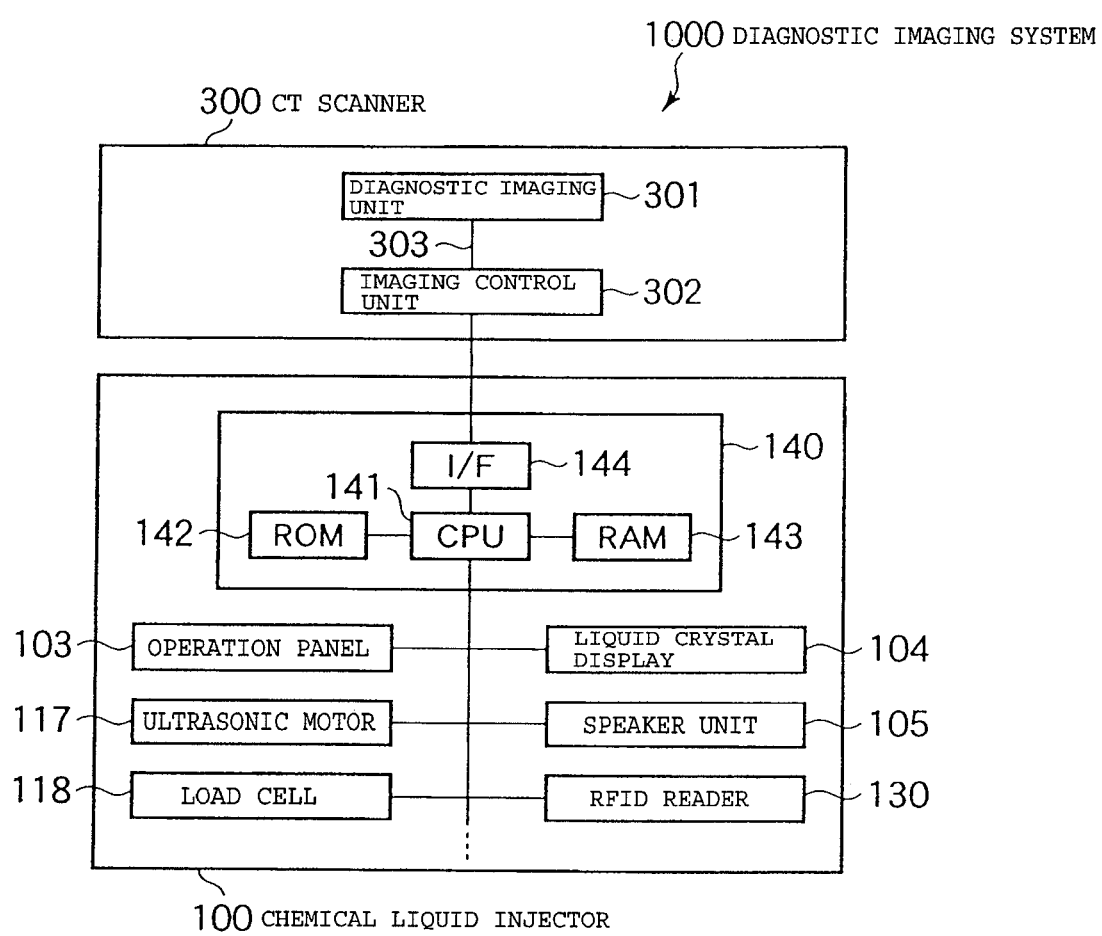
FIG. 12 is a block diagram showing the circuit structure of a chemical liquid injection system.

As shown in FIGS. 11 and 12, CT scanner 300 includes diagnostic imaging unit 301 serving as a mechanism for performing imaging and imaging control unit 302 such that diagnostic imaging unit 301 and imaging control unit 302 are wire-connected through communication network 303. Diagnostic imaging unit 301 shoots diagnostic images of a patient. Imaging control unit 302 controls the operation of diagnostic imaging unit 301.

Figure 8:
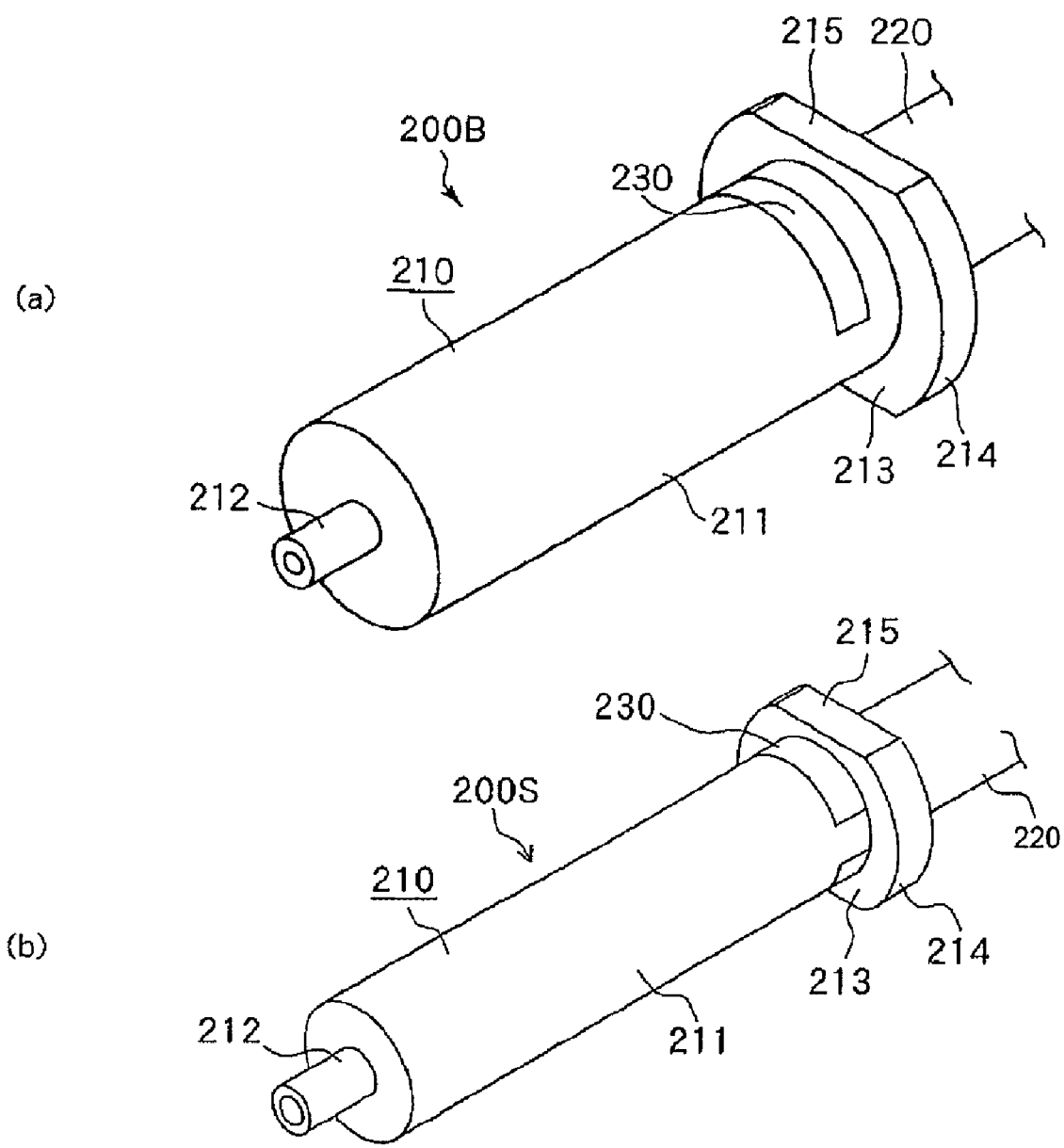
FIG. 8 is a perspective view showing the outer appearance of the chemical liquid syringe.
Figure 9:
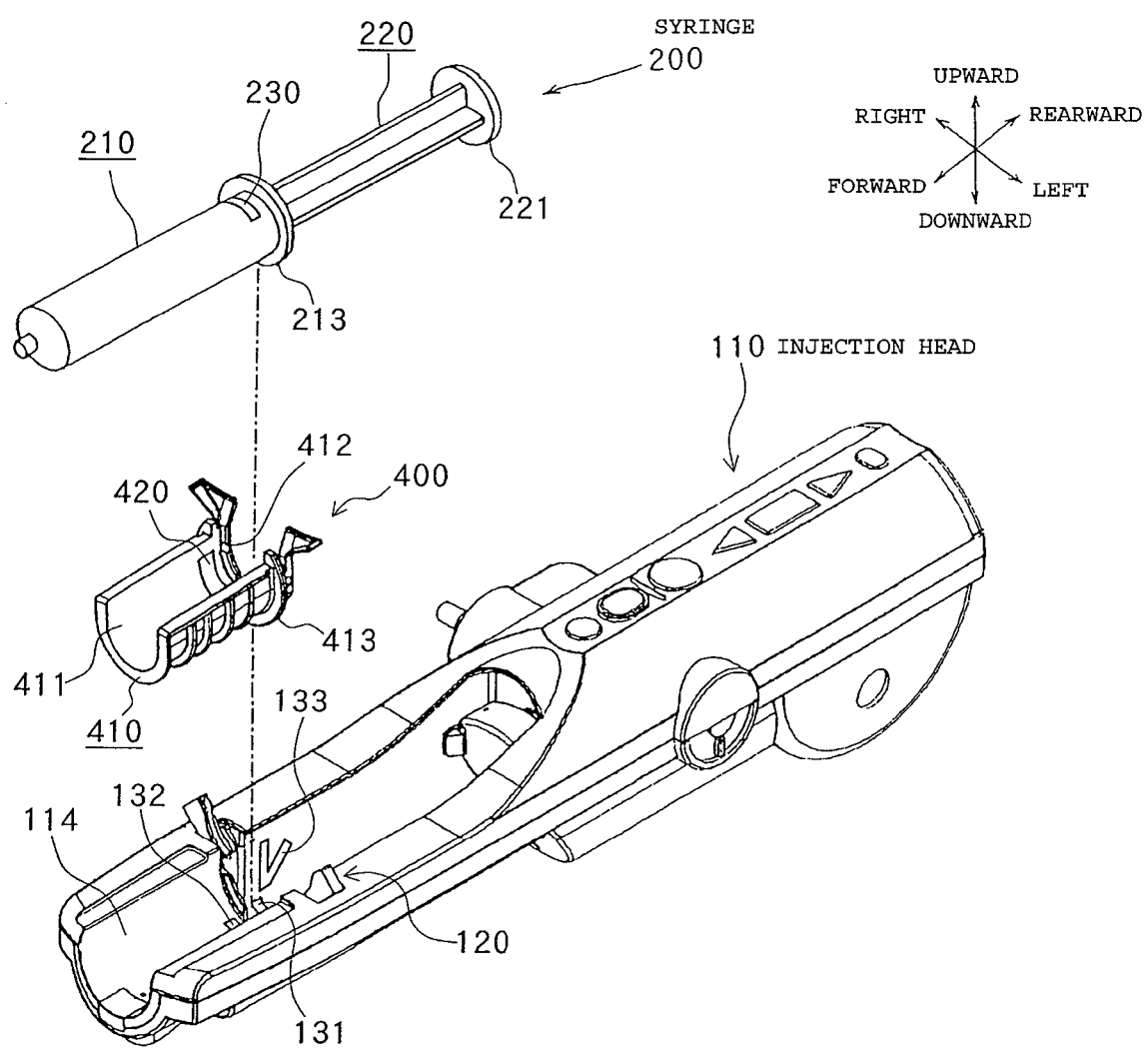
FIG. 9 is a perspective view showing how to mount the chemical liquid syringe on the injection execution head of the chemical liquid injector.

As shown in FIGS. 9 and 8, liquid syringe 200 comprises cylinder member 210 and piston member 220 wherein piston member 220 is slidably inserted into cylinder member 210. Cylinder member 210 includes cylindrical hollow body 211 which has conduit 212 formed at its closed leading end surface.

The trailing end of body 211 of cylinder member 210 is opened, and piston member 220 is inserted from the opening into the interior of body 211. Cylinder member 210 has cylinder flange 213 formed in the outer circumference of the trailing end, and piston member 220 has piston flange 221 formed in the outer circumference of the trailing end.

In chemical liquid injection system 1000 of the embodiment, liquid syringe 200 of the abovementioned structure is interchangeably mounted on chemical liquid injector 100. Liquid syringes 200 of various sizes are used. Chemical liquid injection system 1000 of the embodiment employs liquid syringe 200B of the maximum size directly mounted on chemical liquid injector 100 without using cylinder adapter 400 between them and liquid syringe 200S of a size other than the maximum size mounted on chemical liquid injector 100 by using cylinder adapter 400 between them.

RFID chip 230 is put on cylinder member 210 of liquid syringe 200. RFID chip 230 has various types of data about liquid syringe 200 recorded thereon such as the name, the identification data indicating the pre-filled type or the refill type, the identification data for each item, the capacity, the resistance to pressure of cylinder member 210, the inner diameter of cylinder member 210, and the stroke of piston member 220.

In chemical liquid injection system 1000 of the embodiment, at least some of liquid syringes 200 to be used are of the pre-filled type. Liquid syringe 200 of the pre-filled type is shipped with cylinder member 210 filled with a liquid. When liquid syringe 200 of the pre-filled type is used, RFID chip 230 also has various types of data about the contained liquid recorded thereon such as the name, the ingredients, the viscosity, the expiration date, and the identification data indicating whether the liquid is for CT or MR, as well as the abovementioned various types of data. When a contrast medium is contained as the liquid in liquid syringe 200 of the pre-filled type, RFID chip 230 also has data recorded thereon, as required, such as the various pattern with which the injection rate is changed over time.

Figure 13:
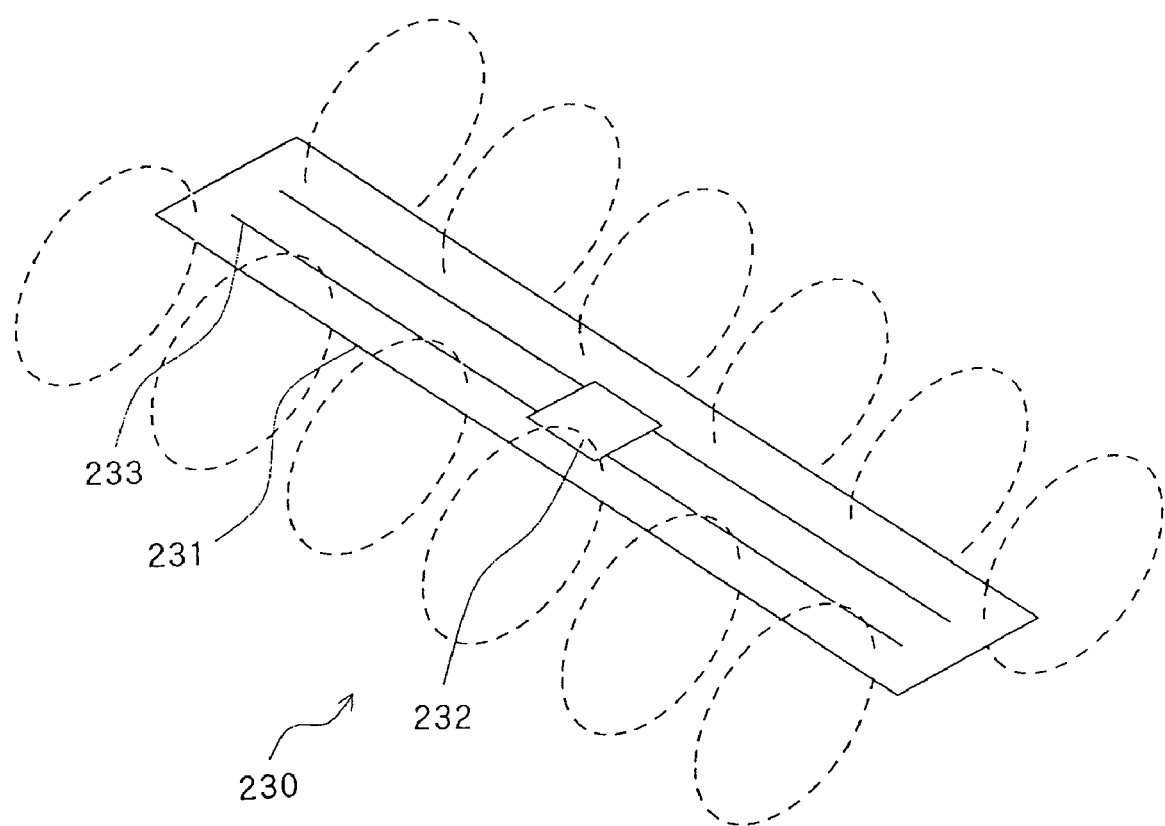
FIG. 13 is a perspective view showing the outer appearance of an RFID chip.

As shown in FIG. 13, RFID chip 230 has chip body 231 formed of an elongated resin sheet and circuit chip 232 included substantially at the center of the sheet. Chip body 231 also has chip antenna 233 formed of printed wiring in a predetermined shape. Circuit chip 232 is mounted on chip antenna 233. For RFID chip 230, a mu chip (registered trademark) with a size of 10×60 (mm) for wireless communication at 2.45 (GHz) is preferably used, for example.

As shown in FIGS. 8 and 9, RFID chip 230 is put on liquid syringe 200 at a position close to cylinder flange 213 of cylinder member 210 such that chip antenna 233 is wound on the outer circumference of cylinder member 210. More specifically, each of liquid syringes 200B and 200S of different sizes includes a pair of flat portions 215 in parallel at opposite positions on annular outer circumference 214 of cylinder flange 213, and as shown in FIG. 8(*a*), in liquid syringe 200B of the maximum size, RFID chip 230 is disposed such that the center thereof is located at one of paired flat portions 215 of cylinder flange 213, and as shown in FIG. 8(*b*), in liquid syringe 200S of the size other than the maximum size, RFID chip 230 is disposed such that the center thereof is located at one of the positions orthogonal to paired flat portions 215 of cylinder flange 213.

Cylinder adapter 400 is provided for each of liquid syringes 200S of sizes other than the maximum size. As shown in FIG. 9, cylinder adapter 400 has generally U-shaped adapter body 410 formed by curving a flat plate. Adapter body 410 is made, for example, of engineering plastic with high strength and does not prevent wireless communication between RFID chip 230 and RFID reader 130, later described.

As also shown in FIGS. 1 to 4, adapter body 410 has concave portion 411 in its upper surface in a semi-cylindrical shape fitting the outer circumference of cylinder member 210 of liquid syringe 200S. Concave groove 412 is formed close to the trailing end of concave portion 411 in the shape fitting cylinder flange 213 of liquid syringe 200S.

On the other hand, the lower surface of adapter body 410 is formed to have the shape and size approximately equal to those of the outer circumference of cylinder member 210 of liquid syringe 200B of the maximum size. Adapter flange 413 is formed close to the trailing end of the lower surface in the shape and size approximately equal to those of cylinder flange 213 of liquid syringe 200B of the maximum size.

Thus, each liquid syringe 200S of a size other than the maximum size can be removably mounted on the cylinder adapter 410 dedicated thereto. Liquid syringe 200S is mounted on cylinder adapter 410 in this manner to allow the shape and size of the portion of cylinder member 210 corresponding to the lower surface to be expanded to the same level as those of liquid syringe 200B of the maximum size.

Figure 10:
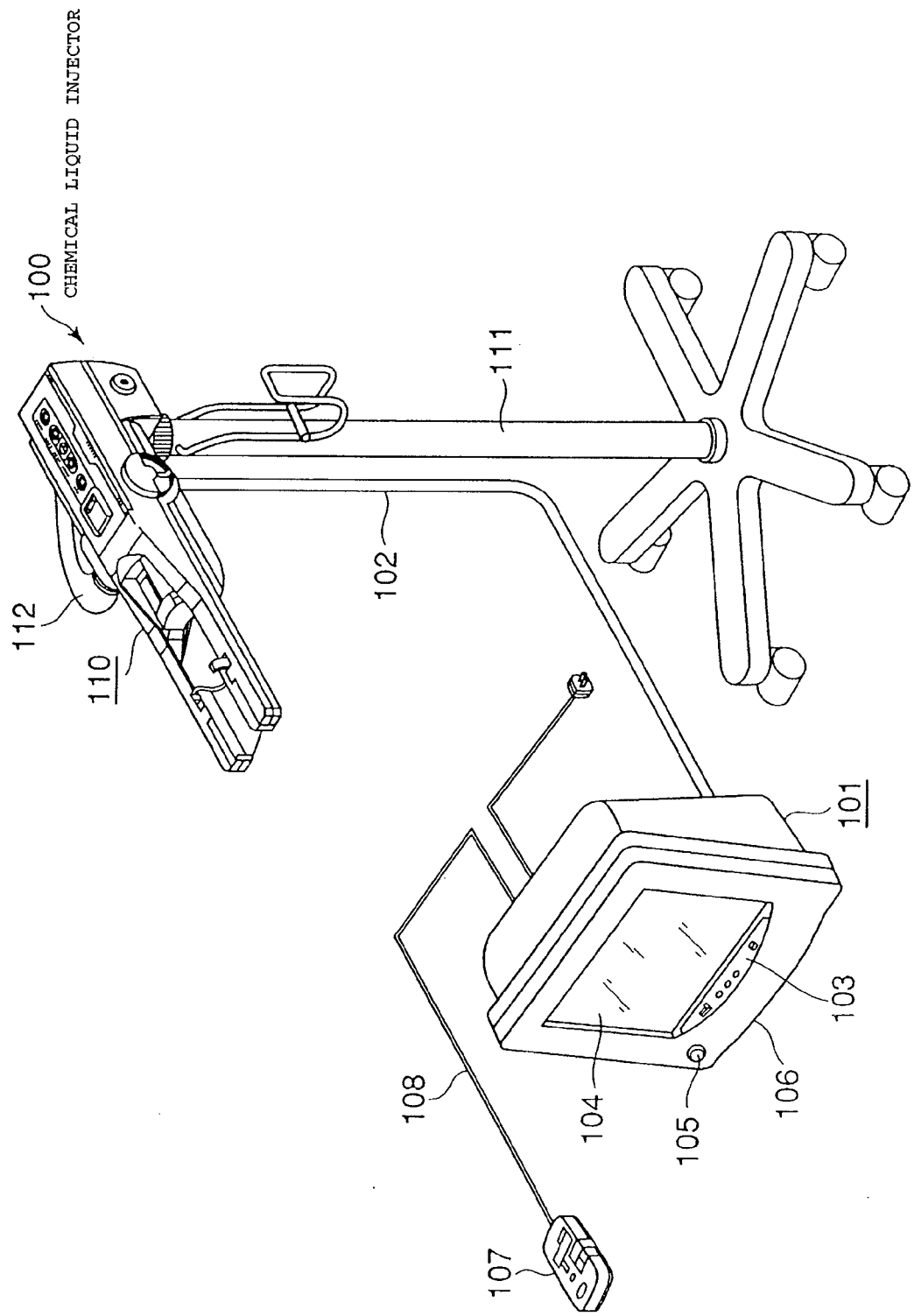
FIG. 10 is a perspective view showing the outer appearance of the chemical liquid injector.

As shown in FIG. 10, chemical liquid injector 100 of the embodiment has injection control unit 101 and injection execution head 110 constructed as separate components which are wire-connected through communication cable 102. Injection execution head 110 is attached to the top end of caster stand 111 by movable arm 112.

As shown in FIG. 9, head body of injection execution head 110 has concave portion 114 formed in its upper surface in a semi-cylindrical shape fitting cylinder member 210 of liquid syringe 200B of the maximum size and adapter body 410 of cylinder 400, and cylinder holding mechanism 120 formed in the forward section of concave portion 114 for removably holding cylinder flange 213 of liquid syringe 200B of the maximum size and adapter flange 413 of cylinder adapter 400.

Figure 3:
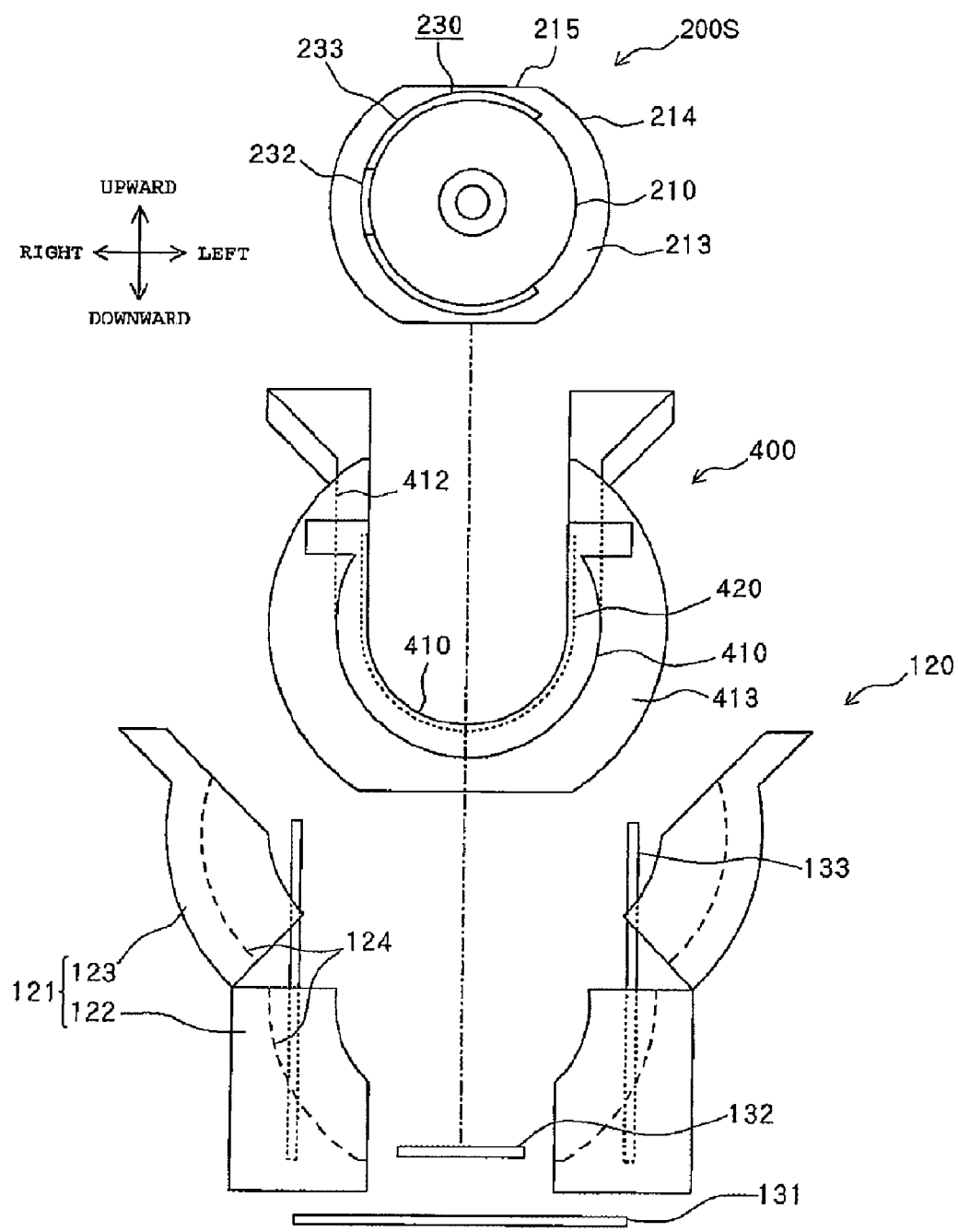
FIG. 3 is a schematic front view showing how to mount the chemical liquid syringe on the chemical liquid injector.
Figure 4:
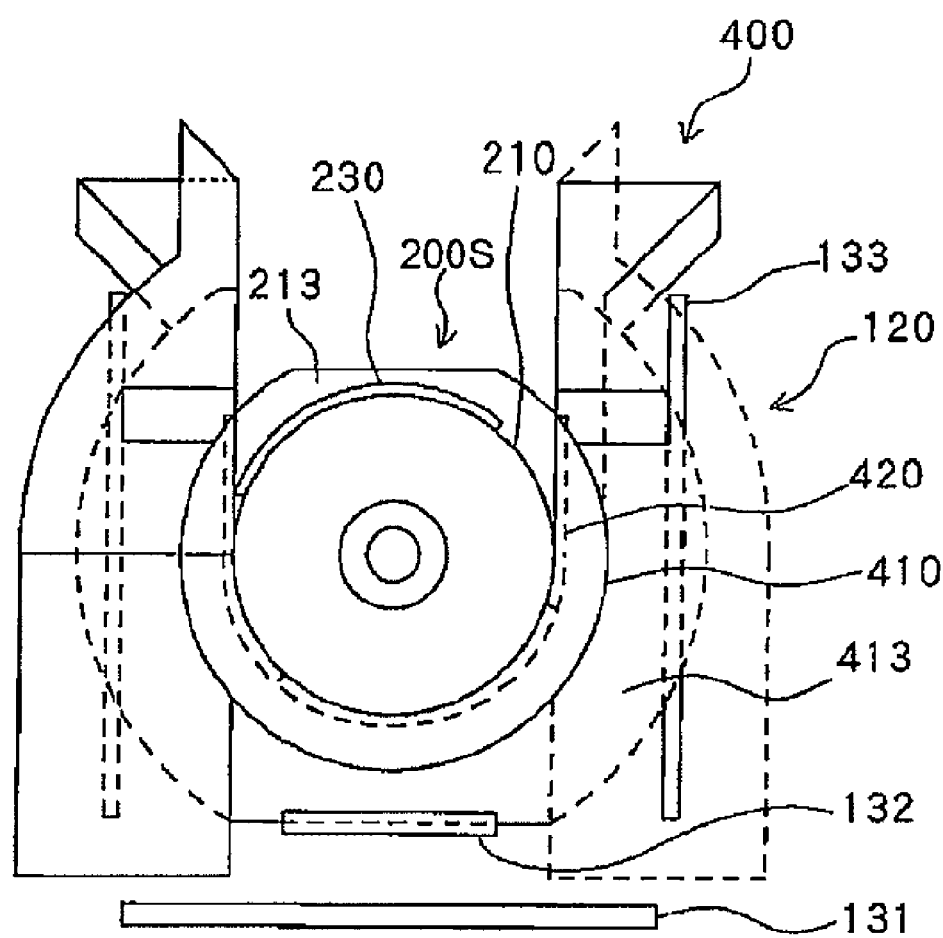
FIG. 4 is a schematic front view showing the chemical liquid syringe mounted on the chemical liquid injector.

More particularly, as shown in FIGS. 3, 4 and the like, cylinder holding mechanism 120 has a pair of flange holding members 121 on the left and right for holding the left and right of cylinder flange 213 of liquid syringe 200B of the maximum size or adapter flange 413 inserted from above.

Flange holding members 121 include fixed holding members 122 and movable holding members 123, both of which are made of high-strength metal such as stainless alloy. Fixed holding members 122 are fixed to the bottom of concave portion 114 of injection execution head 110. Movable holding members 123 are pivoted openably and closeably leftward and rightward at the positions where they are bonded to associated fixed holding members 122 from above. Fixed holding member 122 and movable holding member 123 have arc-shaped concave groove 124 in the inner surfaces. Cylinder flange 213 of liquid syringe 200B of the maximum size or adapter flange 413 is fitted into groove 124.

Figure 5:
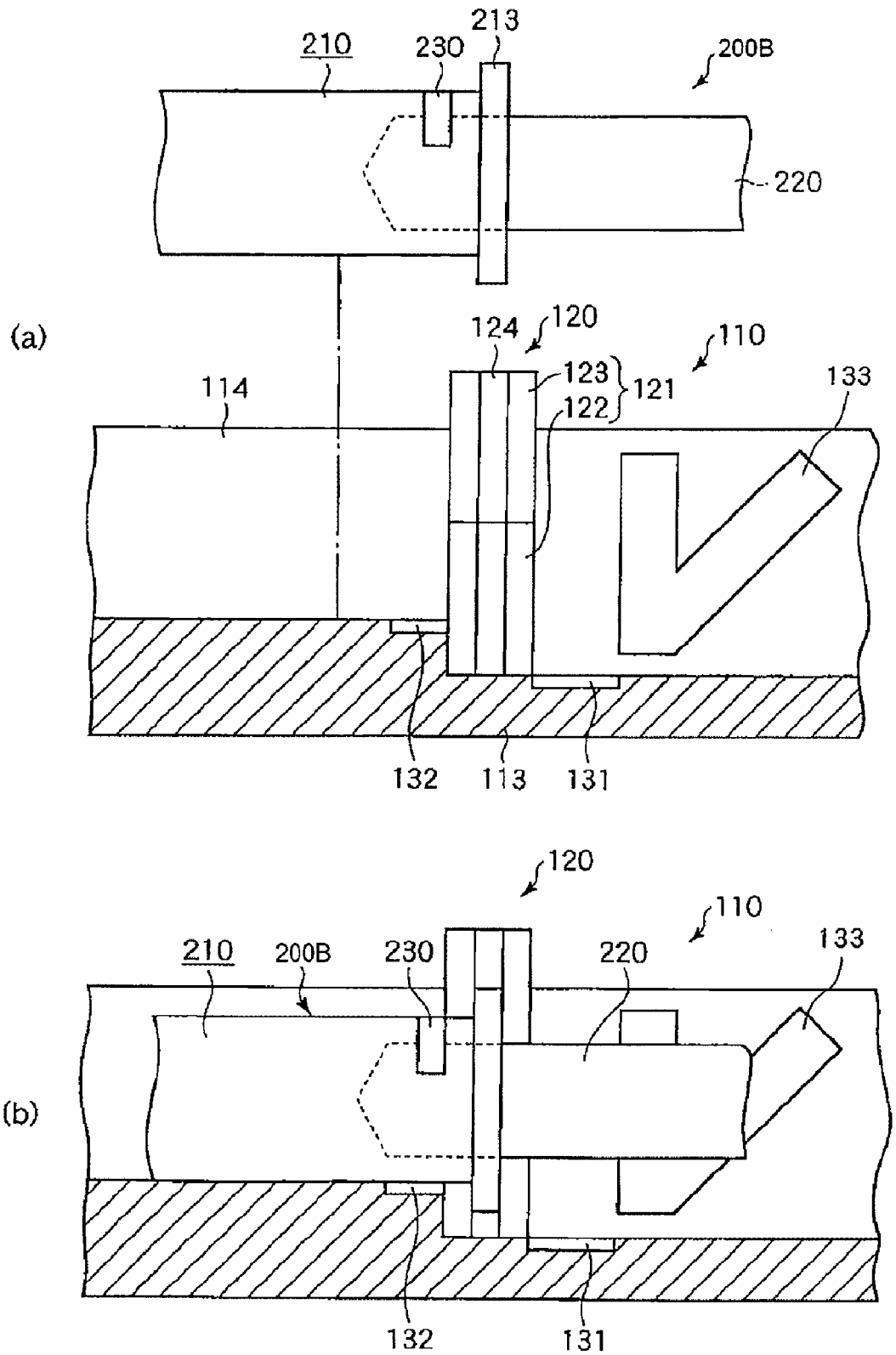
FIG. 5 is a longitudinal section view showing how to mount the chemical liquid syringe on an injection execution head.
Figure 6:
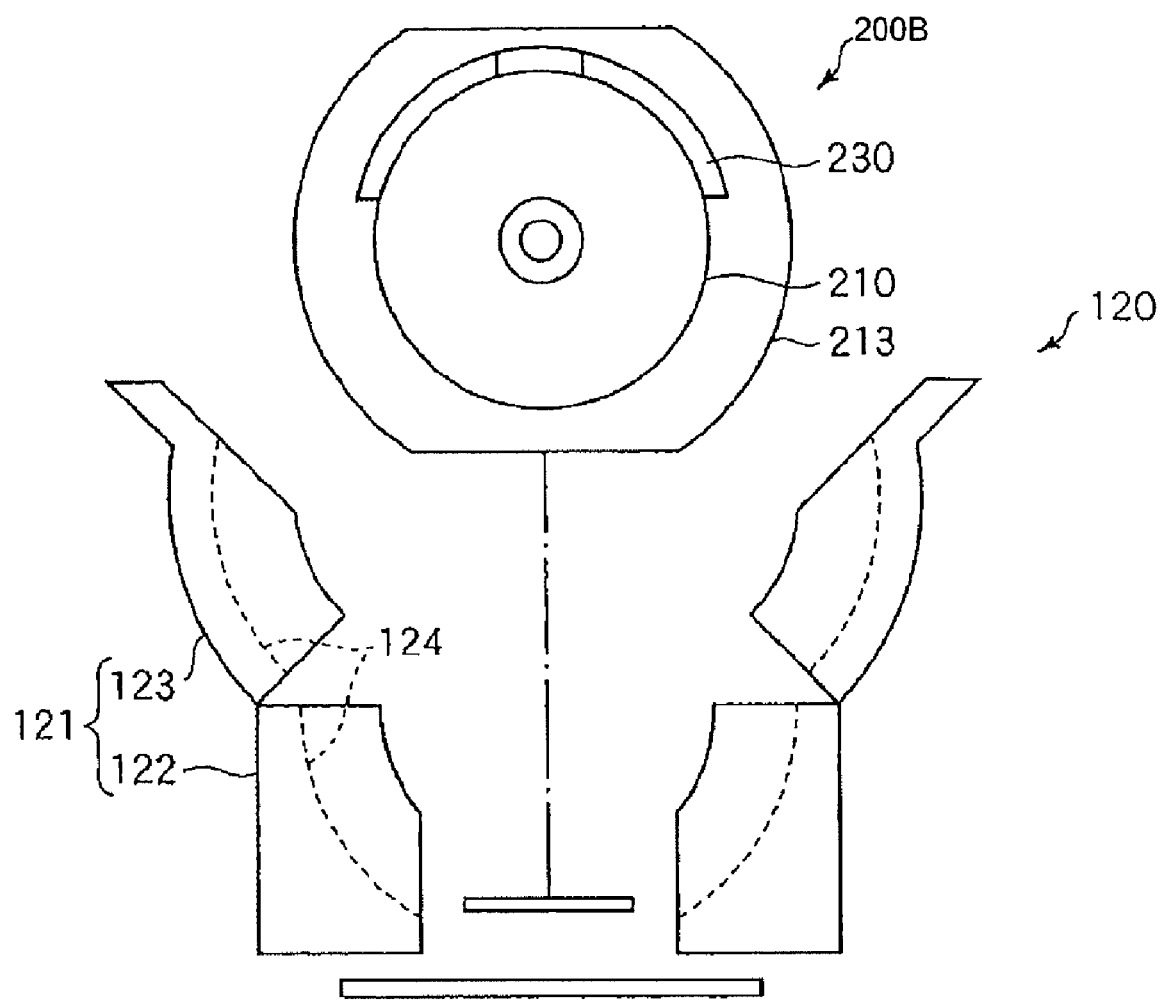
FIG. 6 is a schematic front view showing how to mount the chemical liquid syringe on the chemical liquid injector.
Figure 7:
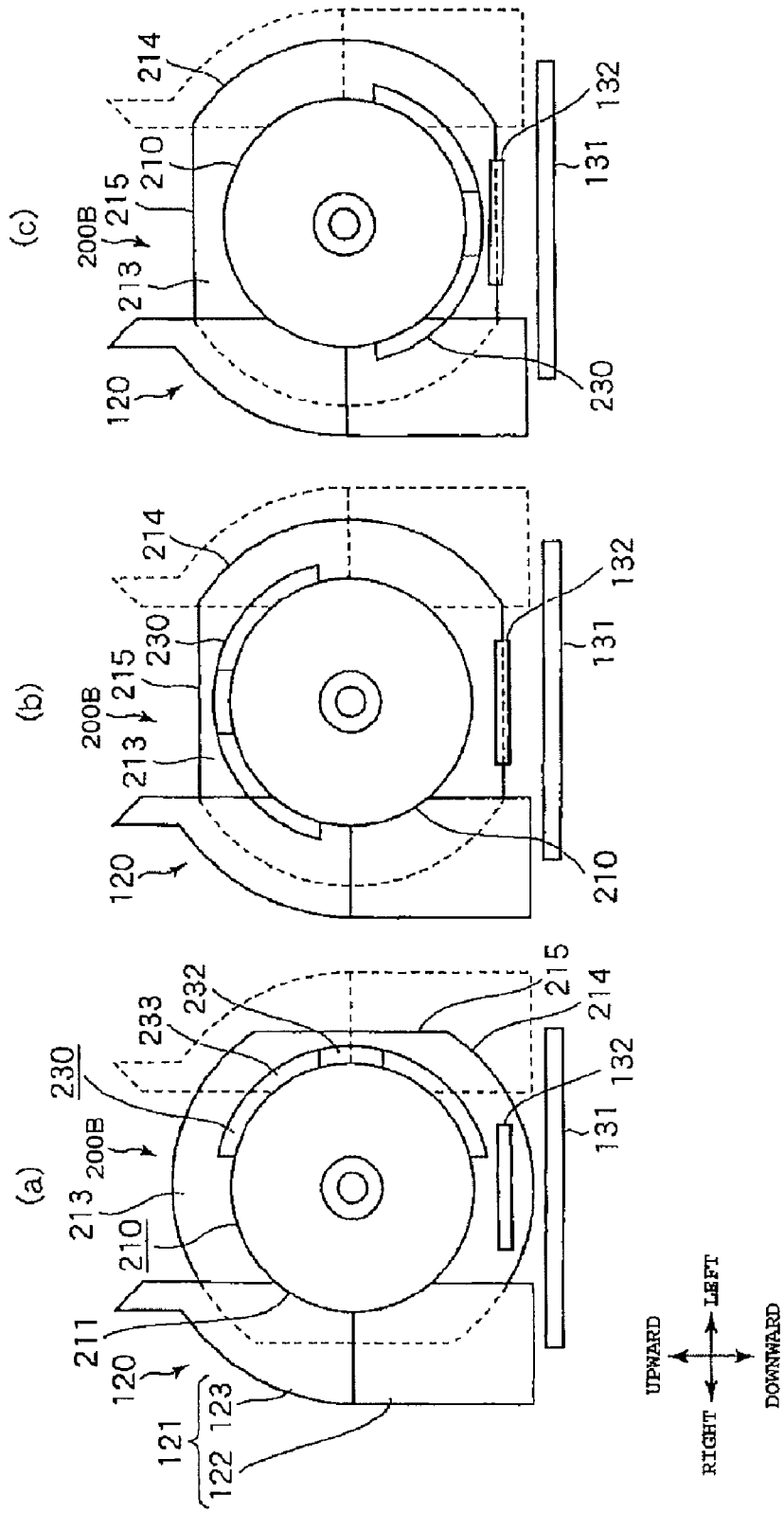
FIG. 7 is a schematic front view showing the chemical liquid syringe mounted on the chemical liquid injector.

Thus, as shown in FIGS. 5 to 7, liquid syringe 200B of the maximum size is removably mounted directly in concave portion 114 and cylinder holding mechanism 120 of injection execution head 110, and as shown in FIGS. 1 to 4, liquid syringe 200S of the size other than the maximum size is removably mounted therein via cylinder adapter 400.

Piston driving mechanism 116 is placed in the rearward section of concave portion 114 of injection execution head 110 for holding and sliding piston flange 221. Piston driving mechanism 116 removably holds piston member 220 of liquid syringe 200 and slides it in the forward and rearward directions.

As shown in FIG. 12, piston holding mechanism 116 has ultrasonic motor 117 as a driving source which is free from generation of magnetic field even in operation, and slides piston member 220 through a screw mechanism (not shown) or the like. Load cell 118 is also contained in piston driving mechanism 116 and detects the pressure applied to piston member 220.

As shown in FIG. 12, chemical liquid injector 100 of the embodiment includes RFID reader 130 which wirelessly communicates with RFID chip 230 on liquid syringe 200 at 2.45 (GHz). RFID reader 130 has a communication circuit (not shown) and reader antenna 131. The communication circuit is contained, for example, in the rearward portion of injection execution head 110.

Figure 2:
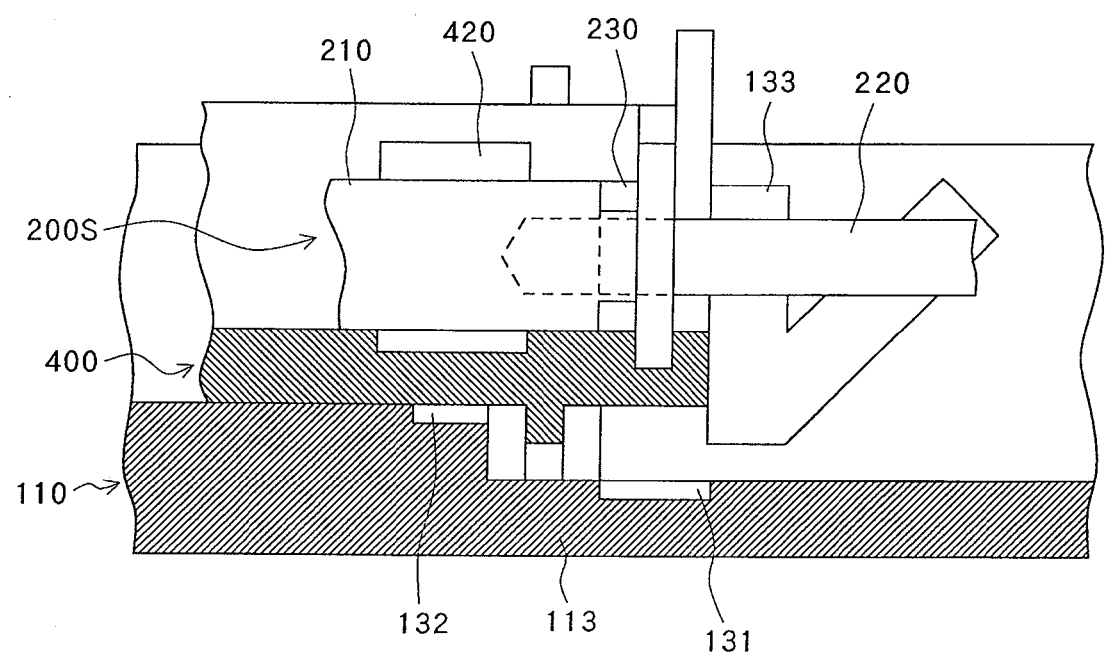
FIG. 2 is a longitudinal section view schematically showing the chemical liquid syringe mounted on the chemical liquid injector.

As shown in FIGS. 3, 4 and the like, reader antenna 131 is formed of an elongated conductor sheet and is connected to the communication circuit. As shown in FIGS. 1, 2 and the like, reader antenna 131 is put on the bottom of concave portion 114 at a position at the rear of cylinder holding mechanism 120 and is placed such that its longitudinal direction corresponds to the left-to-right direction.

Chemical liquid injector 100 of the embodiment has auxiliary antenna 132 and resonance antenna 133 in addition to reader antenna 131 of RFID reader 130. Auxiliary antenna 132 is formed of an elongated conductor sheet shorter and smaller than reader antenna 131 and is not connected to the communication circuit.

Auxiliary antenna 132 is put on the bottom of concave portion 114 at a position immediately in front of cylinder holding mechanism 120 and is disposed such that its longitudinal direction corresponds to the left-to-right direction. FRID chip 230 is placed at a position in front of cylinder flange 213 of liquid syringe 200 of the maximum size. As shown in FIG. 5, when liquid syringe 200B of the maximum size is held by cylinder holding mechanism 120, auxiliary antenna 132 is placed immediately below chip antenna 233.

As shown in FIGS. 1 and 2, interfering conductor 420 in an elongated sheet shape longer and larger than reader antenna 131 is put on cylinder adapter 400 at a position overlapping auxiliary antenna 132 in the state in which cylinder adapter 400 is held by cylinder holding mechanism 120. Concave groove 412 for holding cylinder flange 213 is located sufficiently at the rear of adapter flange 413 held by cylinder holding mechanism 120.

RFID chip 230 is placed at the position immediately in front of cylinder flange 213 of liquid syringe 200S of the size other than the maximum size. When liquid syringe 200S of the size other than the maximum size is held by cylinder adapter put in cylinder holding mechanism 120, chip antenna 233 is located at the rear of flange holding member 121.

A pair of resonance antennas 133 is formed on the left and right symmetrically with respect to a plane, and is mounted on the left and right internal surfaces of concave portion 114 at positions at the rear of cylinder holding mechanism 120. Each resonance antenna 133 has body portion 134 formed of conductor elongated in the vertical direction and inclined portion 135 formed of elongated conductor inclined such that its upper end is located at the rear of its lower end. Body portion 134 and inclined portion 135 are connected to each other at their lower ends.

In chemical liquid injection system 1000 of the embodiment, RFID chip 230 wirelessly communicates with RFID reader 130 at a frequency of "2.45 (GHz)" as described above, with a wavelength of approximately "122 (mm)" and one-half wavelength of approximately "61 (mm)". Chip antenna 233, reader antenna 131, and portions 134, 135 of resonance antenna 133 are formed to have the overall length of "60 (mm)" corresponding to the abovementioned half wavelength. Paired resonance antennas 133 on the left and right are spaced from each other by the interval of approximately "60 (mm)" corresponding to the abovementioned half wavelength. On the other hand, auxiliary antenna 132 is formed to have the overall length of "30 to 40 (mm)", for example, sufficiently smaller than the abovementioned half wavelength. Interfering conductor 420 is formed to have the overall length of "60 (mm)" corresponding to the abovementioned half wavelength.

At least when liquid syringe 200 is mounted on chemical liquid injector 100, the leading end of piston member 220 is placed at the trailing end of cylinder member 210. As shown in FIGS. 1 and 5, RFID chip 230 is put on the outer circumference of the trailing end of cylinder member 210 at the position overlapping the leading end of piston member 220.

Since chemical liquid injector 100 of the embodiment is formed as the structure provided by adding RFID reader 130 and the like to an existing product, the arrangement of injection execution head 110 or the like is not changed from the existing product. Thus, concave portion 114 of injection execution head 110 is formed in the semi-cylindrical shape fitting cylinder member 210 of liquid syringe 200 in front of cylinder holding mechanism 120, but its bottom face in the rearward portion is located downward for favorable assembly of cylinder holding mechanism 120. Injection execution head 110 contains a metal frame (not shown) in front of auxiliary antenna 132 in concave portion 114.

As shown in FIG. 12, injection control unit 101 connected to injection execution head 110 formed as described above through communication cable 102 contains a computer unit 140 and is wire-connected to imaging control unit 302 of CT scanner 300 through communication network.

As shown in FIG. 10, injection control unit 101 has operation panel 103, liquid crystal display 104 serving as a data display means, and speaker unit 105, all of which are disposed on the front face of unit housing 106. Injection control unit 101 is wire-connected to controller unit 107 as a separate component through connector 108.

Referring again to FIG. 12, in chemical liquid injector 100 of the embodiment, the abovementioned various devices are connected to computer unit 140 which integrates and controls those various devices. Computer unit 140 has a so-called one-chip microcomputer provided with hardware such as CPU (Central Processing Unit) 141, ROM (Read Only Memory) 142, RAM (Random Access Memory) 143, I/F (Interface) 144 and the like. Computer unit 140 has an appropriate computer program installed as firmware or the like on an information storage medium such as ROM 142, and CPU 141 executes various types of processing in accordance with the computer program.

Figure 14:
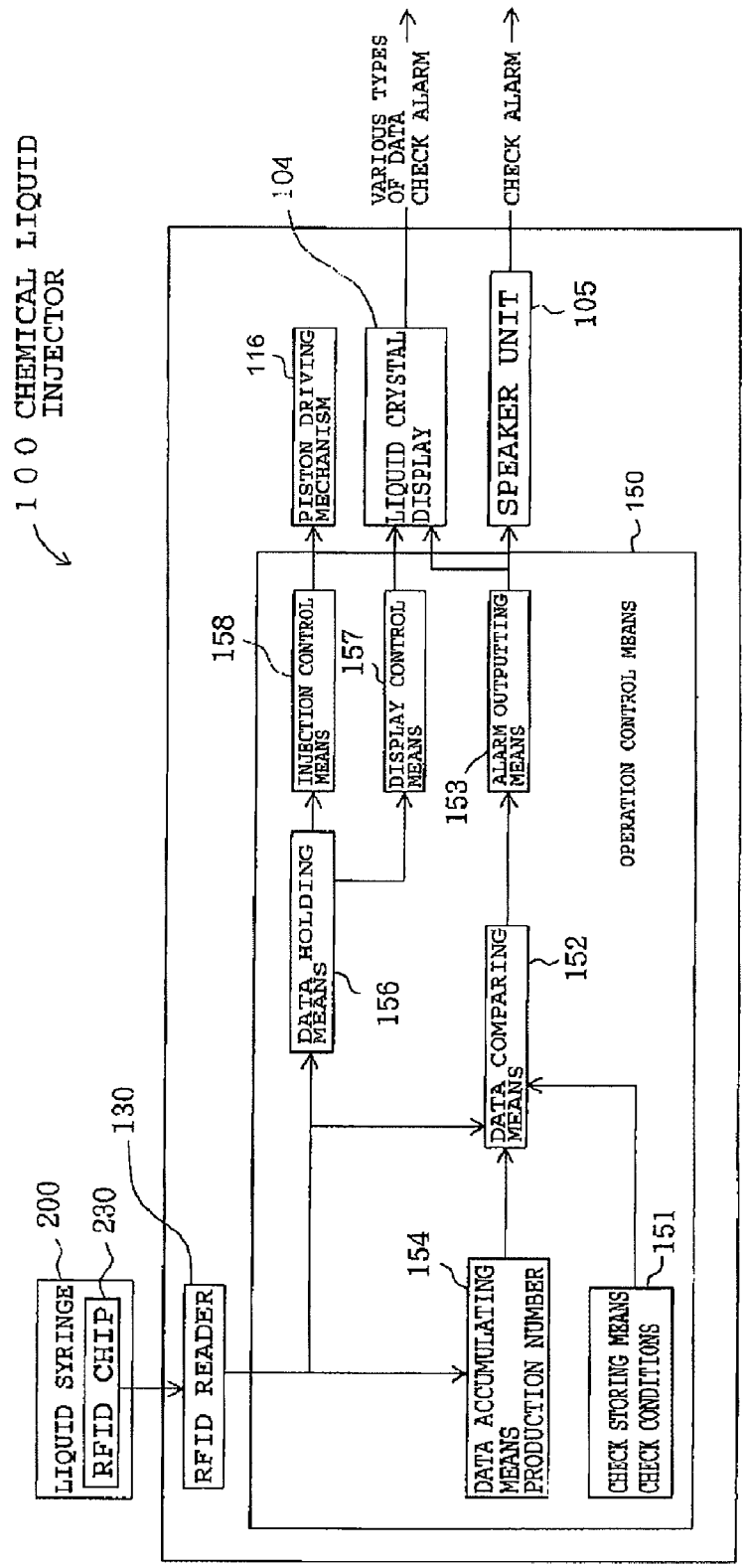
FIG. 14 is a schematic block diagram showing the logical structure of the chemical liquid injector.

In chemical liquid injector 100 of the embodiment, computer unit 140 operates in accordance with the computer program installed as described above to logically have operation control means 150 as shown in FIG. 14. Operation control means 150 logically includes various means such as check storing means 151, data comparing means 152, alarm outputting means 153, data accumulating means 154, data holding means 156, display control means 157, and injection control means 158.

Operation control means 150 corresponds to the function of CPU 141 which performs predetermined operations in accordance with the computer program installed in ROM 142 or the like and the various types of data wirelessly received from RFID chip 230.

Check storing means 151 corresponds to the store area of RAM 143 and the like recognized by CPU 141 and stores data on predetermined check conditions. Data comparing means 152 compares the stored data on check conditions with the various types of data wirelessly received from RFID chip 230. Alarm outputting means 153 outputs and notifies a check alarm in accordance with the comparison result.

More particularly, RAM 143 has data for identifying usable liquid syringes 200 registered thereon in the check conditions. When RFID reader 130 wirelessly receives various types of data from RFID chip 230 of liquid syringe 200, the wirelessly received identification data of liquid syringe 200 is compared with the identification data registered in RAM 143.

When the wirelessly received identification data does not match the registered data, a guidance message, for example "This product not registered as usable device. Check if it is usable" is output as a check alarm with display on liquid crystal display 104 and with sound from speaker unit 105.

The current date and time is constantly updated and held in the check conditions on RAM 143. When the expiration date is wirelessly received from RFID chip 230 of liquid syringe 200, the expiration date is compared with the current date and time. If the current data and time is after the expiration date, a guidance message, for example "Expiration date of this product elapsed. Use new one" is output as a check alarm with display on liquid crystal display 104 and with sound from speaker unit 105.

The production number of each liquid syringe 200 of the pre-filled type is set on RFID chip 230. Data accumulating means 154 stores the data of the production number of liquid syringe 200 of the pre-filled type put on injection execution head 110 and used to perform injection operation.

Data comparing means 152 compares the stored production numbers with the production number wirelessly received from RFID chip 230. When a match is found between the compared production numbers, alarm outputting means 153 outputs a guidance message, for example "This pre-filled syringe used previously. Use new one" as a check alarm with display on liquid crystal display 104 and with sound from speaker unit 105.

Data holding means 156 holds various types of data wirelessly received from RFID chip 230. Display control means 157 displays the held various types of data on liquid crystal display 104. Injection control means 158 controls the operation of piston driving mechanism 116 based on the held various types of data.

More specifically, RFID chip 230 of liquid syringe 200 has various types of data recorded thereon such as the name, the resistance to pressure, and the capacity of liquid syringe 200 as well as the name, the ingredients, and the expiration date of the liquid contained in liquid syringe 200. The various types of data are temporarily stored in RAM 143 and output with display on liquid crystal display 104.

When the control data for piston driving mechanism 116 is set on RFID chip 230 of liquid syringe 200, the control data is held in RAM 143, and CPU 141 controls the operation of piston driving mechanism 116 based on the held control data.

For example, when a various pattern for changing the injection rate of the contrast medium with time is recorded as data on RFID chip 230 of liquid syringe 200, CPU 141 changes the operation rate of piston driving mechanism 116 over time in accordance with the variable pattern. When the resistance to pressure is recorded as data on RFID chip 230 of liquid syringe 200, CPU 141 controls the operation of piston driving mechanism 116 such that the resistance to pressure held as data in RAM 143 is not exceeded based on the pressure detected by load cell 118. When the capacity is recorded as data on RFID chip 230 of liquid syringe 200, CPU 141 controls the operation of piston driving mechanism 116 based on the capacity held as data on RAM 143.

Although the abovementioned various means of chemical liquid injector 100 are accomplished by pieces of hardware such as liquid crystal display 104 as required, they are mainly implemented by CPU 141 as a piece of hardware functioning in accordance with the resources and the computer program stored on an information storage medium such as ROM 142.

Such a computer program is stored on an information storage medium such as RAM 143 as software for causing CPU 141 or the like to perform processing operations including comparing the check conditions stored as data in RAM 143 and the like with the various types of data wirelessly received from RFID chip 230 when RFID reader 130 wirelessly receives the various types of data from RFID chip 230, outputting the check alarm with data display on liquid crystal display 104 in accordance with the comparison result, storing the production number of liquid syringe 200 mounted and used to perform injection operation in RAM 143 or the like, comparing the stored production numbers with the production number wirelessly received from RFID chip 230, outputting the check alarm with data display on liquid crystal display 104 in accordance with the comparison result, holding the various types of data wirelessly received from RFID chip 230 on RAM 143 or the like, displaying the held various types of data on liquid crystal display 104, and controlling the operation of piston driving mechanism 116 in accordance with the held various types of data.

Operation of the Embodiment

When chemical liquid injection system 1000 of the embodiment is used in the abovementioned structure, injection execution head 110 of chemical liquid injector 100 is placed near diagnostic imaging unit 301 of CT scanner 300, and liquid syringe 200 or the like is prepared for use as shown in FIG. 11.

For example, when liquid syringe 200B of the maximum size is used, an operator opens movable holding members 123 of injection execution head 110 and puts liquid syringe 200B of the maximum size in concave portion 114 to insert cylinder flange 213 into movable holding members 123 and then closes movable holding members 123.

When liquid syringe 200B of the maximum size is appropriately mounted such that flat portions 215 of cylinder flange 213 are located at the top and bottom as shown in FIGS. 7(b) and 7(c), RFID chip 230 is located at the top or bottom of liquid syringe 200. The longitudinal direction of chip antenna 233 of RFID chip 230 is substantially in parallel with the longitudinal directions of reader/auxiliary antennas 131, 132 of RFID reader 130, so that RFID chip 230 wirelessly communicates with RFID reader 130.

If liquid syringe 200B of the maximum size is inappropriately mounted such that flat portions 215 of cylinder flange 213 are located on the left and right as shown in FIG. 7(a), RFID chip 230 is located on the left or right of liquid syringe 200. Since the longitudinal direction of chip antenna 233 of RFID chip 230 is not in parallel with the longitudinal directions of reader/auxiliary antennas 131, 132 of RFID reader 130, RFID chip 230 does not communicate wirelessly with RFID reader 130.

The underlying principles will be described in brief. RFID chip 230 wirelessly communicates with RFID reader 130 through an electric field (radio wave communication) and a magnetic field (magnetic coupling), and now attention is focused on the magnetic field to simplify the description. As shown in FIG. 13, chip antenna 233 of RFID chip 230 is formed in the elongated linear shape, so that the magnetic field is produced cylindrically with its longitudinal direction as the center of axis.

Since each of reader/auxiliary antennas 131, 132 of RFID reader 130 is also formed in the elongated linear shape, the magnetic field is produced cylindrically with its longitudinal direction as the center of axis. Thus, chip antenna 233 and reader/auxiliary antennas 131, 132 are favorably coupled magnetically when they are placed in parallel, but when they are not placed in parallel, they are not satisfactorily coupled magnetically.

For this reason, in chemical liquid injection system 1000 of the embodiment, when liquid syringe 200B of the maximum size is appropriately mounted on chemical liquid injector 100 such that flat portions 215 of cylinder flange 213 are located at the top and bottom as shown in FIGS. 7(b) and 7(c), RFID chip 230 wirelessly communicates with RFID reader 130. However, if liquid syringe 200B of the maximum size is inappropriately mounted on chemical liquid injector 100 such that flat portions 215 of cylinder flange 213 are located on the left and right as shown in FIG. 7(a), RFID chip 230 does not wirelessly communicate with RFID reader 130.

On the other hand, when liquid syringe 200S of the size other than the maximum size is used, for example, the operator opens movable holding members 123 of injection execution head 110 and puts cylinder adapter 400 in concave portion 114 to insert adapter flange 413 into movable holding members 123 and then closes movable holding members 123.

Chemical liquid injector 100 and cylinder adapter 400 are designed specifically to each other and have a concave and a convex or the like which engage with each other (not shown). Thus, cylinder adapter 400 is appropriately mounted on chemical liquid injector 100 at all times. Liquid syringe 200S of the size other than the maximum size is removably mounted on cylinder adapter 400 put in chemical liquid injector 100 in this manner.

When liquid syringe 200S of the size other than the maximum size is appropriately mounted such that flat portions 215 of cylinder flange 213 are located at the top and bottom as shown in FIGS. 1 to 4, RFID chip 230 is located on the left or right. The longitudinal direction of chip antenna 233 of RFID chip 230 is substantially in parallel with the longitudinal directions of body portions 134 of paired resonance antennas 133, so that paired resonance antennas 133 produce resonance of a radio signal from RFID chip 230.

Since resonance antennas 133 include inclined portions 135 inclined at a predetermined angle, the radio signal resonated and amplified by paired resonance antennas 133 is favorably received by reader antenna 130 to allow wireless communication between RFID chip 230 and RFID reader 130.

As described above, when RFID chip 230 on liquid syringe 200B of the maximum size is located on the left or right, RFID chip 230 cannot communicate wirelessly with RFID reader 130. This is because cylinder holding mechanism 120 holds the left and right portions of cylinder flange 213 of liquid syringe 200B of the maximum size with paired cylinder holding members 121 as shown in FIGS. 5 and 6, so that the wireless communication of RFID chip 230 located on the left or right is prevented by metallic cylinder holding members 121.

On the other hand, as shown in FIGS. 1 and 2, RFID chip 230 on liquid syringe 200S of the size other than the maximum size is located sufficiently at the rear of cylinder holding mechanism 120, and resonance antennas 133 and reader antenna 131 are located at the rear of cylinder holding mechanism 120. RFID chip 230 wirelessly communicates with RFID reader 130 via resonance antennas 133 without being prevented by metallic cylinder holding members 121.

When liquid syringe 200S of the size other than the maximum size is inappropriately mounted such that flat portions 215 of cylinder flange 213 are located on the left and right, RFID chip 230 is located at the top or bottom. In this case, since the longitudinal direction of chip antenna 233 is not substantially in parallel with the longitudinal direction of resonance antennas 133, the wireless communication between RFID chip 230 and RFID reader 130 is not amplified by the resonance of resonance antennas 133.

In this case, the longitudinal directions of chip antenna 233 and reader/auxiliary antennas 131, 132 are substantially in parallel. However, interfering conductor 420 overlaps auxiliary antenna 132, so that the wireless communication between RFID chip 230 and RFID reader 130 is not assisted by auxiliary antenna 132.

As shown in FIGS. 3 and 4, in liquid syringe 200S of the size other than the maximum size, chip antenna 233 which should be placed flatly is extremely curved and the communication performance thereof is reduced. Thus, even when the longitudinal directions of chip antenna 233 and reader antenna 131 are substantially in parallel, RFID chip 230 does not communicate wirelessly with RFID reader 130 if the auxiliary functions of auxiliary antenna 131 and resonance antennas 133 are not provided.

In chemical liquid injection system 1000 of the embodiment, when liquid syringe 200S of the size other than the maximum size is appropriately mounted on chemical liquid injector 100 with cylinder adapter 400 such that flat portions 215 of cylinder flange 213 are located at the top and bottom as shown in FIGS. 1 to 4, RFID chip 230 wirelessly communicates with RFID reader 130. However, when liquid syringe 200S of the size other than the maximum size is inappropriately mounted such that flat portions 215 of cylinder flange 213 are located on the left and right, RFID chip 230 does not wirelessly communicate with RFID reader 130.

The present inventor prototyped liquid syringes 200B, 200S of various sizes, cylinder adapter 400, and chemical liquid injector 100 as described above, and tested the directivity of RFID reader/chip 130, 230 by rotating liquid syringe 200B of the maximum size mounted on injection execution head 110.

Figure 15:
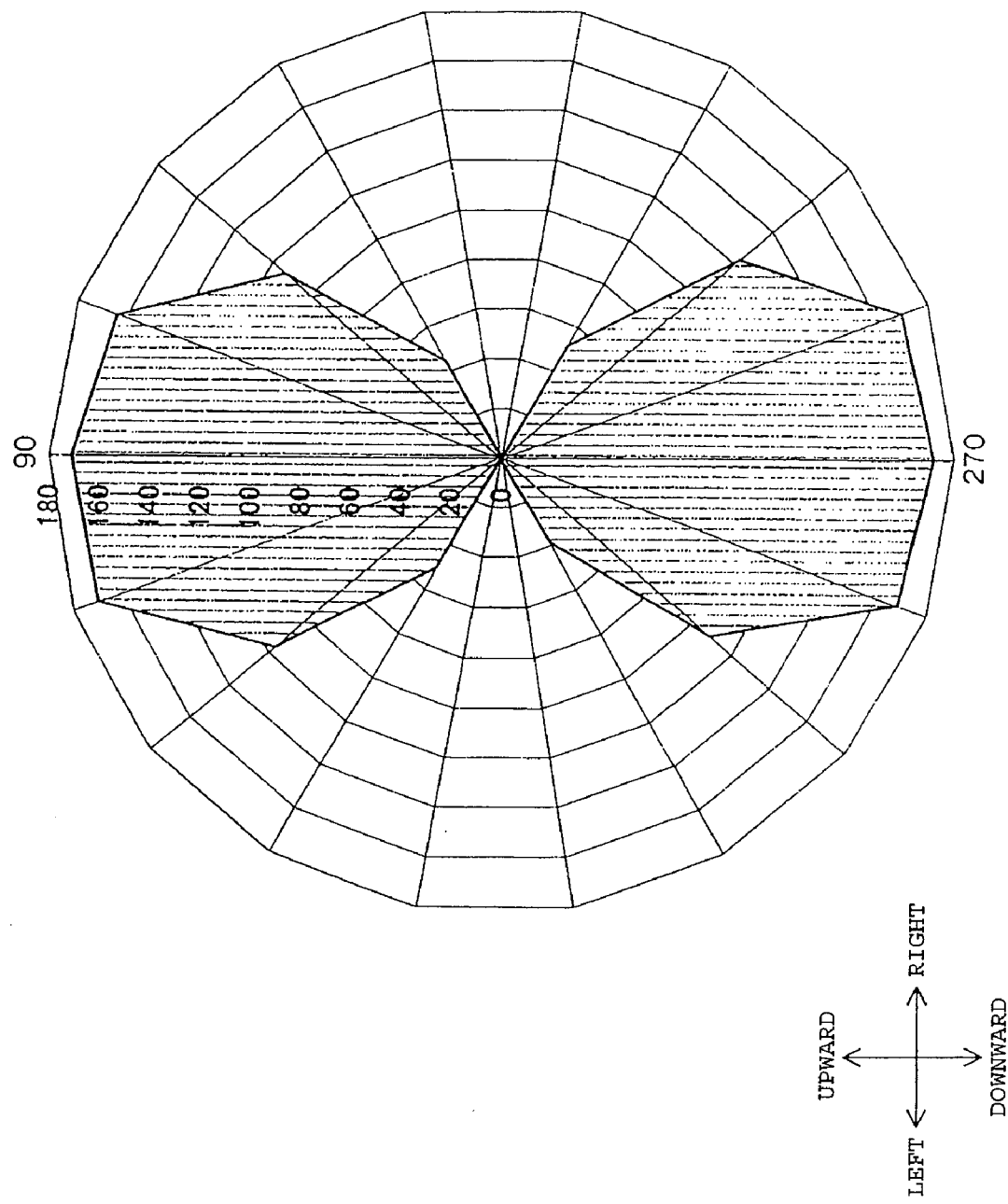
FIG. 15 is a diagram showing the relationship between the rotation angle of the chemical liquid syringe and the communication sensitivity of the RFID chip/reader.

As shown in FIG. 15, the sensitivity of communication between RFID chip 230 and RFID reader 130 was at the maximum when RFID chip 230 was located at the top or bottom, and was substantially "zero" when RFID chip 230 was located on the left or right.

When liquid syringe 200S of the size other than the maximum size was mounted with cylinder adapter 400 on injection execution head 110 and rotated, the sensitivity of communication between RFID chip 230 and RFID reader 130 was at the maximum when RFID chip 230 was located on the left or right, and was substantially "zero" when RFID chip 230 was located at the top or bottom.

The sensitivity of communication between RFID reader 130 and RFID chip 230 of liquid syringe 200S of the size other than the maximum size was measured when resonance antenna 133 formed of body portion 134 and inclined portion 135 was mounted, only body portion 134 was mounted, and when only inclined portion 135 was mounted in injection execution head 110. It was found that favorable wireless communication was possible only when resonance antenna 133 formed of body portion 134 and inclined portion 135 was used.

In addition, RFID chip 230 of liquid syringe 200S of the size other than the maximum size was located immediately above auxiliary antenna 132 without mounting interfering conductor 420 on cylinder adapter 400. However, RFID chip 230 did not communicate wirelessly with RFID reader 130. It was shown that this was because chip antenna 233 which should be placed flatly was extremely curved to reduce the communication performance as described above.

Figure 16:
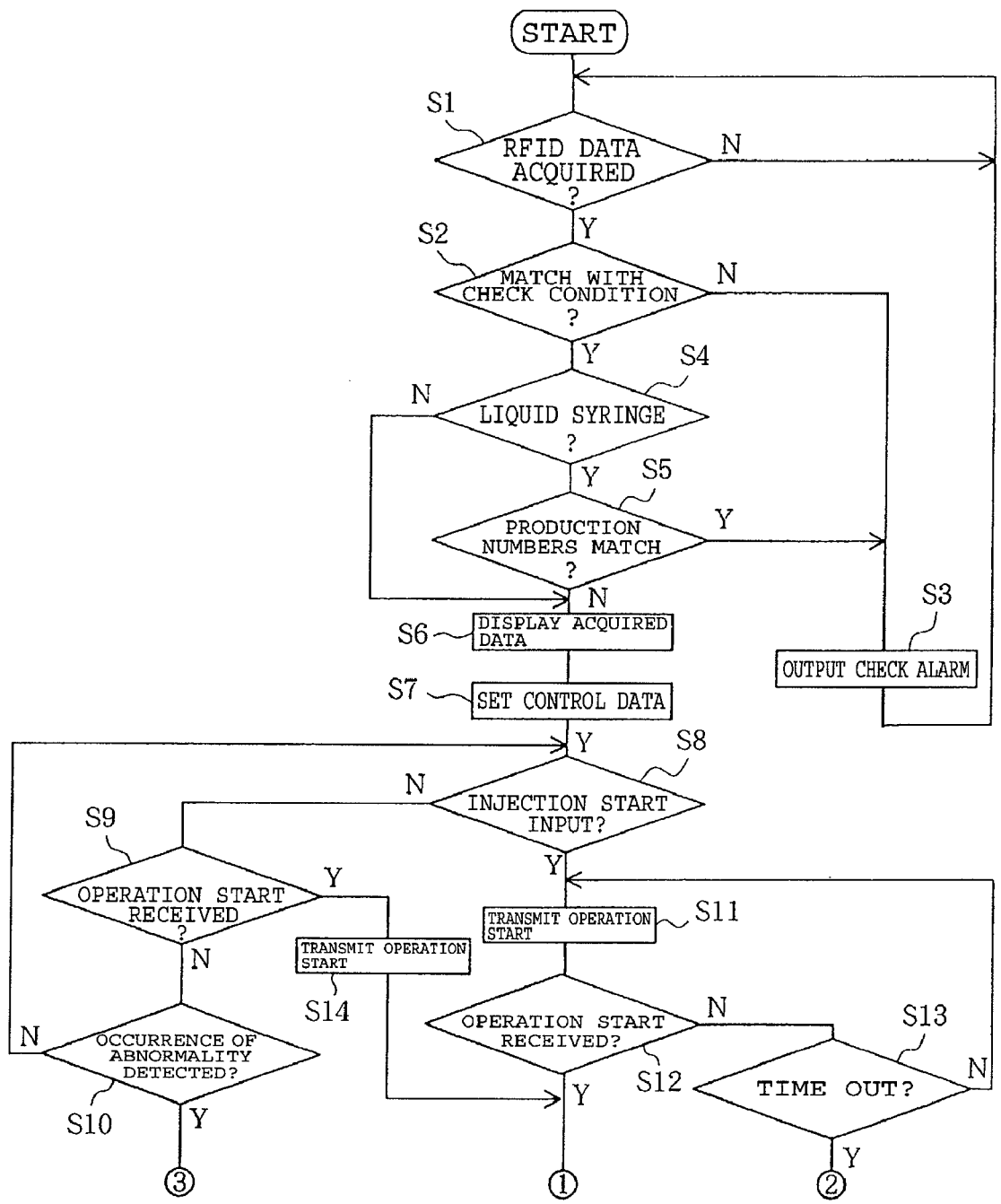
FIG. 16 is a flow chart showing the first half of processing operation in the chemical liquid injector.

Referring to FIG. 16, in chemical liquid injector 100 of the embodiment, when liquid syringe 200 is appropriately mounted on injection execution head 110 to wirelessly receive various types of data from RFID chip 230 by RFID reader 130 (step S1), computer unit 140 compares the received data with the check conditions registered on RAM 143 (step S2).

Such check conditions include the identification data of usable liquid syringes 200. If the identification data wirelessly received from RFID chip 230 is not included in the registered check conditions, a guidance message, for example "This product not registered as usable device. Check if is usable" is output as a check alarm with display on liquid crystal display 104 and with sound from speaker unit 105 (step S3).

When liquid syringe 200 is appropriately mounted on injection execution head 110, RFID chip 230 is naturally faced toward RFID reader 130 of injection execution head 110 with a predetermined interval between them, so that various types of data on RFID chip 230 are wirelessly received by RFID reader 130 (step S1).

The wirelessly received data is compared with the check conditions (step S2), and a check alarm is output (step S3) if the wirelessly received identification data is not included in the check conditions. After the data matches the check conditions, when it is determined that the device to be used is liquid syringe 200 (step S4), the production number wirelessly received from RFID chip 230 is compared with the production number registered in RAM 143 (step S5).

When the compared production numbers match, a guidance message, for example "This syringe used previously. Use new one" is output as a check alarm on liquid crystal display 104 and from speaker unit 105 (step S3).

The various types of data wirelessly received from RFID chip 230 of the appropriate device into chemical liquid injector 100 as described above are output with display on liquid crystal display 104, for example as "Contrast medium syringe (name) made by (manufacturer) mounted. Production number XXX, name of liquid XXX, type of liquid XXX, capacity XXX, resistance to pressure XXX" (step S6).

RFID chip 230 has various types of data to be displayed and various types of data not to be displayed. For example, a binary flag is set in each data to indicate whether or not the data should be displayed. Chemical liquid injector 100 appropriately selects some of the various types of data wirelessly received from RFID chip 230 for display.

When the various types of data wirelessly received from RFID chip 230 of the device into chemical liquid injector 100 include control data such as "resistance to pressure," "capacity," and "variable pattern for changing the injection rate of the contrast medium over time," then the control data is set in RAM 143 of computer unit 140 (step S7). When such control data is not included in the data wirelessly received from RFID chip 230, default control data is set.

Liquid syringe 200 thus mounted on chemical liquid injector 100 is connected to a patient through an extension tube (not shown) or the like and then the operator makes entry to start operation to operation panel 103. Chemical liquid injector 100 detects the entry (step S8) and transmits data for starting operation to CT scanner 300 (step S11).

Figure 18:
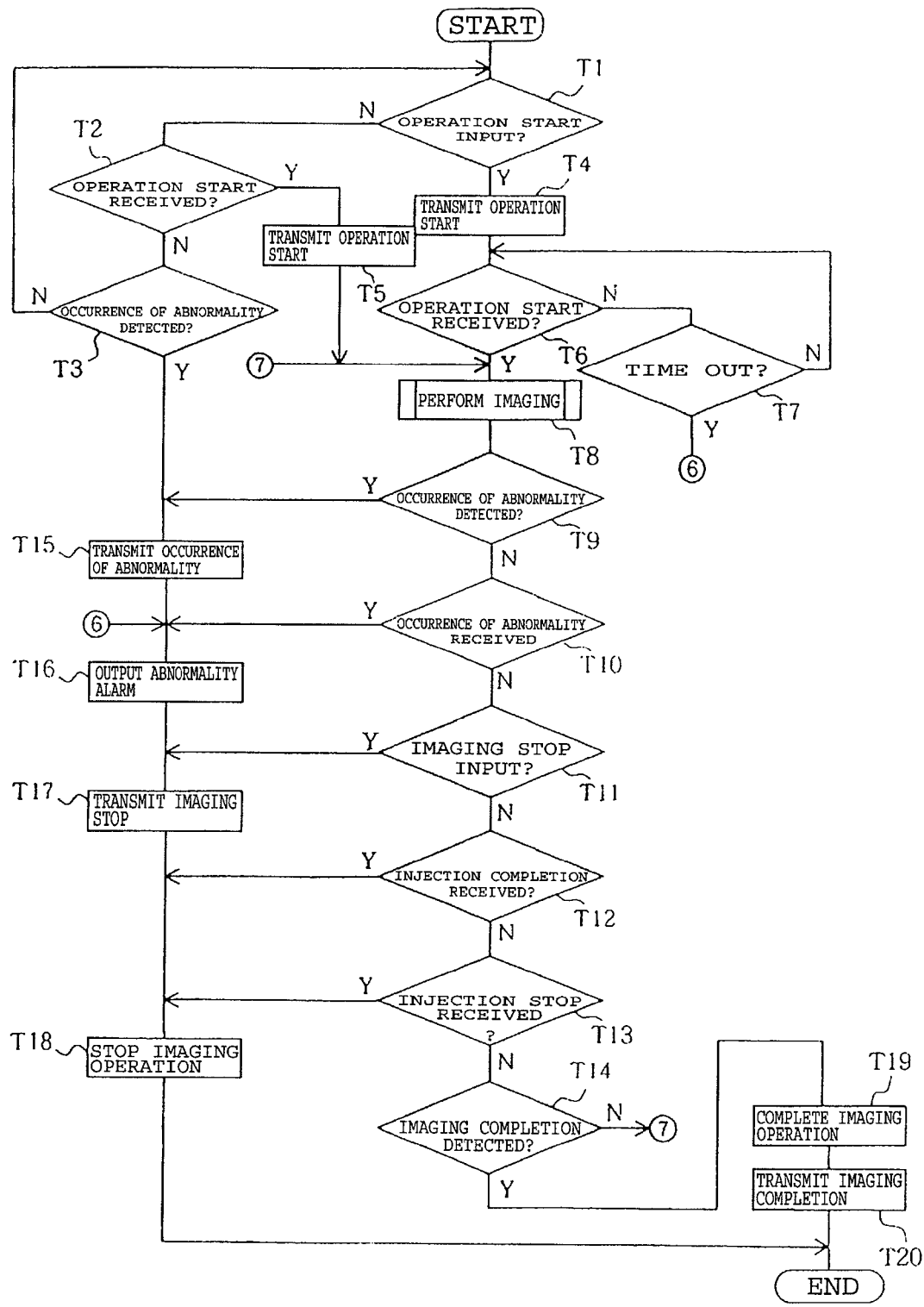
FIG. 18 is a flow chart showing processing operation in the CT scanner.

Referring to FIG. 18, CT scanner 300 receives the data for staring operation from chemical liquid injector 100 (step T2) and transmits the data for starting operation back to chemical liquid injector 100 and performs imaging operation (step T8). Thus, in diagnostic imaging system 1000 of the embodiment, the imaging of CT scanner 300 follows the liquid injection of chemical liquid injector 100.

As shown in FIGS. 16 and 18, in diagnostic imaging system 1000 of the embodiment, when chemical liquid injector 100 is ready as described above (steps S8 to S10) and the operator makes entry to start operation to CT scanner 300 (step T1), the liquid injection of chemical liquid injector 100 follows the imaging of CT scanner 300 (steps T4, T6-, steps S9, S18-).

Figure 17:
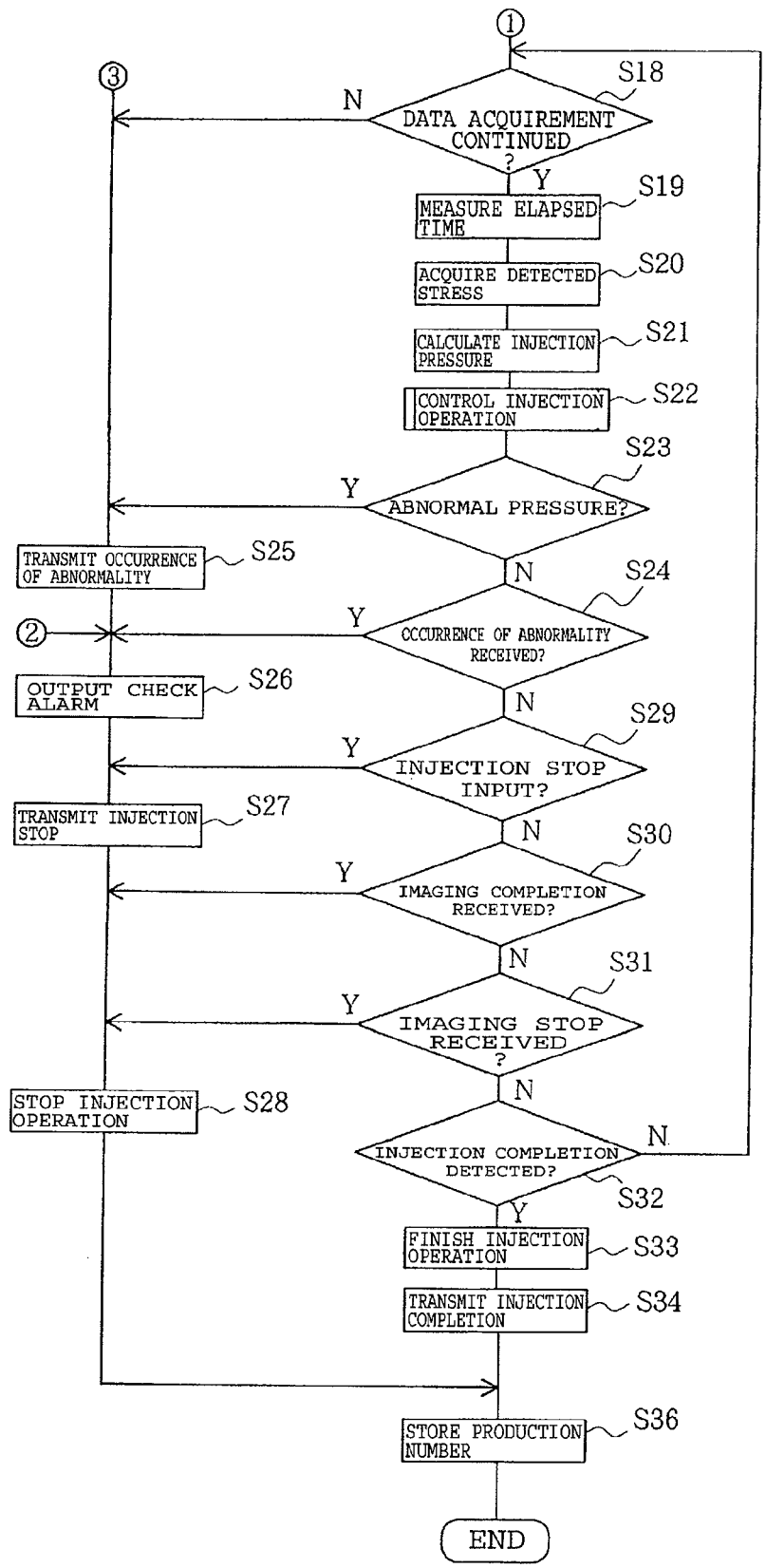
FIG. 17 is a flow chart showing the latter half.

Referring to FIG. 17, when a series of liquid injection operations is performed (step S18-) in chemical liquid injector 100 of the embodiment, the elapsed time from the start of the injection is measured (step S19), and the operation of piston driving mechanism 116 is controlled in real time based on the elapsed time and the control data wirelessly received from RFID chip 230 (step S22).

When the variable pattern for changing the injection rate of the contrast medium over time is set in RFID chip 230 of liquid syringe 200, the operation rate of piston driving mechanism 116 is changed with time in accordance with the variable pattern. When piston driving mechanism 116 is driven as described above, the stress detected by load cell 118 is wirelessly received in real time by computer unit 140 (step S20).

The injection pressure of the liquid is calculated from the stress detected by load cell 118 (step S21) based on the viscosity of the liquid, the inner diameter of cylinder member 210 and the like wirelessly received from RFID chip 230. The operation of piston driving mechanism 116 is controlled in real time such that the calculated injection pressure satisfies the pressure range wirelessly received from RFID chip 230 (step S23). Thus, when the resistance to pressure is set on RFID chip 230 of liquid syringe 200, the operation of piston driving mechanism 116 is controlled in accordance with the resistance to pressure.

While liquid syringe 200 is driven by piston driving mechanism 116 as described above, RFID chip 230 on liquid syringe 200 is continuously detected by RFID reader 130 (step S18). If the abovementioned detection is stopped (step S18) before the completion of the injection operation (step S32), the injection operation performed by piston driving mechanism 116 is stopped (step S28).

In addition, a guidance message, for example "Syringe removal detected. Make sure syringe put appropriately" is output as a check alarm with display on liquid crystal display 104 and with sound from speaker unit 105 (step S26). The occurrence of abnormality and the stop of injection are transmitted as data to CT scanner 300 (steps S25 and S28).

Then, CT scanner 300 receives the data representing the occurrence of abnormality (step T10) and outputs the occurrence of abnormality as a check alarm with guidance display or the like (step T16). When it receives the data representing the stop of operation (step T13), the imaging operation is stopped (step T18).

In chemical liquid injector 100 and CT scanner 300 of the embodiment, when the occurrence of abnormality is detected in the abovementioned ready state (steps S10 and T3) or when the occurrence of abnormality is detected during the operation (steps S23 and T9), the occurrence of abnormality is output and notified (steps S26 and T16) and the operation is stopped (steps S28 and T18).

Since the occurrence of abnormality in one of them is transmitted to the other (steps S25 and T15), the other receives the data (steps T10 and S24) and then outputs and notifies the occurrence of abnormality (steps T16 and S26). Since the operation stop in one of them is transmitted to the other (steps S27 and T17), the other receives the data (steps T13 and S31) and stops the operation (steps T18 and S28).

When one of them receives entry to stop operation (steps S29 and T11), the one stops the operation (steps S28 and T18) and transmits it to the other (steps S27 and T17). The other receives the data (steps T13 and S31) and stops the operation (steps T18 and S28).

When the completion of the operation is detected in one of them (steps S32 and T14), the operation is ended (steps S33 and T19) and the end of the operation is transmitted to the other (steps S34 and T20). The other receives the data (steps T12 and S31) and stops the operation (steps T18 and S28).

In chemical liquid injector 100 of the embodiment, when the injection operation is finished normally or abnormally as described above (steps S33 and S28), the identification data wirelessly received from RFID chip 230 of liquid syringe 200 is registered as the check condition in RAM 143 (step S36).

Effect of the Embodiment

In chemical liquid injection system 1000 of the embodiment, RFID chip 230 having the various types of data recorded thereon is placed on liquid syringe 200 as described above. Chemical liquid injector 100 wirelessly receives the various types of data from RFID chip 230 and performs the predetermined operation in accordance with at least some of the various types of data. In this manner, a large amount of data can be easily entered into chemical liquid injector 100 to perform various operations.

In chemical liquid injection system 1000 of the embodiment, only when liquid syringe 200 is appropriately held by cylinder holding mechanism 120, RFID chip 230 wirelessly communicates with RFID reader 130. Only when RFID chip 230 wirelessly communicates with RFID reader 130 in this manner, the operation of piston driving mechanism 116 is permitted. This can automatically prevent piston member 220 from being pressed into cylinder member 210 in the state in which liquid syringe 200 is not appropriately held.

In chemical liquid injector 100 of the embodiment, computer unit 140 allows piston driving mechanism 116 to operate only when RFID reader 130 detects RFID chip 230. If liquid syringe 200 comes off the appropriate position during the liquid injection, the liquid injection operation can be stopped automatically.

Since the mechanism for detecting the appropriate mounting of liquid syringe 200 is formed of RFID chip/reader 230 and 130 for transmitting the various types of data from liquid syringe 200 to chemical liquid injector 100, the appropriate mounting of liquid syringe 200 can be detected by using the simple structure without requiring a dedicated sensor mechanism.

In chemical liquid injection system 1000 of the embodiment, liquid syringes 200B and 200S of various sizes can be used, and the operator can check if each of the syringes is mounted at an appropriate angle on injection execution head 110. Since the wireless communication of RFID chip 230 is prevented by liquid, RFID chip 230 needs to be placed near the trailing end of cylinder member 210 where the liquid is not contained.

As shown in FIG. 5, since cylinder flange 213 at the trailing end of cylinder member 210 of liquid syringe 200B of the maximum size is directly held by flange holding mechanism 120 of injection execution head 110, RFID chip 230 cannot be placed at the rear of metallic flange holding mechanism 120.

Thus, when liquid syringe 200B of the maximum size is held by flange holding mechanism 120 and RFID chip 230 is placed on the side, the wireless communication of RFID chip 230 is prevented by metallic flange holding mechanism 120. However, as shown in FIGS. 5 and 7, RFID chip 230 on liquid syringe 200B of the maximum size of the embodiment is located at the top or bottom while it is appropriately held by flange holding mechanism 120, so that RFID chip 230 can wirelessly communicate with RFID reader 130 favorably.

Especially for liquid syringe 200B of the maximum size, RFID chip 230 wound and put on the outer circumference of cylinder member 210 is not extremely curved and thus the communication performance is not prevented. Even when reader antenna 131 is located at the rear of RFID chip 230 on liquid syringe 200B of the maximum size held by flange holding mechanism 120, the wireless communication can be performed favorably by auxiliary antenna 132 located immediately below RFID chip 230.

On the other hand, liquid syringe 200S of the size other than the maximum size is held by flange holding mechanism 120 with cylinder adapter 400 between them as shown in FIGS. 1 and 2, so that RFID chip 230 cannot be located in front of metallic flange holding mechanism 120. Since RFID chip 230 is extremely curved to reduce the communication performance, it cannot wirelessly communicate with RFID reader 130 if it is located at the top of liquid syringe 200S held by cylinder adapter 400 in flange holding mechanism 120.

In chemical liquid injector 100 of the embodiment, however, paired resonance antennas 133 on the left and right are placed at the rear of flange holding mechanism 120, and RFID chip 230 on liquid syringe 200S of the size other than the maximum size is located on the side when liquid syringe 200S is appropriately held by flange holding mechanism 120. RFID chip 230 can wirelessly communicate with RFID reader 130 favorably.

Cylinder adapter 400 includes interfering conductor 420 located at the position overlapping auxiliary antenna 132. Even when RFID chip 230 on liquid syringe 200 of the size other than the maximum size held by cylinder adapter 400 in flange holding mechanism 120 is located at the bottom, RFID chip 230 and RFID reader 130 do not wirelessly communicate with each other uselessly.

In chemical liquid injection system 1000 of the embodiment, reader antenna 131 is located at the rear of flange holding mechanism 120 together with resonance antennas 133 in order to wirelessly communicate with RFID chip 230 on liquid syringe 200S of the size other than the maximum size located at the rear of metallic flange holding mechanism 120.

On the other hand, RFID chip 230 on liquid syringe 200B of the maximum size is located in front of flange holding mechanism 120. Since auxiliary antenna 132 is located in front of flange holding mechanism 120, RFID chip 230 on liquid syringe 200B of the maximum size can wirelessly communicate with RFID reader 130 favorably.

As described above, paired resonance antennas 133 on the left and right are located at the rear of flange holding mechanism 120 in order to achieve favorable wireless communication between RFID chip 230 on liquid syringe 200S of the size other than the maximum size and RFID reader 130 when RFID chip 230 is located on the side. Since RFID chip 230 on liquid syringe 200B of the maximum size is located in front of metal flange holding mechanism 120, it does not communicate wirelessly with RFID reader 130 uselessly even when it is located on the side.

The wireless communication between RFID reader 130 and RFID chip 230 is inhibited by liquid as described above. As shown in FIG. 5, the leading end of piston member 220 is located at the trailing end of cylinder member 210 in liquid syringe 200, and RFID chip 230 is mounted on the outer circumference of the trailing end of cylinder member 210 at the position overlapping the leading end of piston member 220.

Thus, RFID chip 230 is not placed at a position overlapping the liquid contained in cylinder member 210 in chemical liquid injection system 1000 of the embodiment, so that RFID chip 230 and RFID reader 130 can favorably perform wireless communication without being inhibited by the liquid.

The present inventor has confirmed that the a conductor shorter and smaller than reader/chip antennas 131, 233 does not prevent the wireless communication between RFID chip/reader 230, 130 and can favorably relay the communication, but a conductor equal to or longer and larger than reader/chip antennas 131, 233 prevents the wireless communication between RFID chip/reader 230, 130.

For this reason, auxiliary antenna 132 is formed to be shorter and smaller than reader/chip antennas 131, 233 and favorably assists the wireless communication between RFID reader 130 and RFID chip 230 on liquid syringe 200B of the maximum size. Interfering conductor 420 is formed to have the overall length equal to that of reader/chip antennas 131, 233 and satisfactorily prevents useless wireless communication between RFID reader 130 and RFID chip 230 on liquid syringe 200S of the size other than the maximum size.

Since resonance antenna 133 has body portion 134 extending vertically and inclined portion 135 having the upper end inclined rearward, it can favorably assist the wireless communication between RFID reader 130 and RFID chip 230 on liquid syringe 200S of the size other than the maximum size. In addition, paired resonance antennas 133 on the left and right are spaced from each other by the distance substantially corresponding to the half wavelength in the wireless communication between RFID reader/chip 130, 230, so that it can resonate the communication signal between RFID reader/chip 130, 230 to amplify the signal favorably.

Furthermore, in chemical liquid injection system 1000 of the embodiment, at least some of the various types of data wirelessly received from RFID chip 230 are held as data and output with display on liquid crystal display 104, so that the operator can check the various types of data of liquid syringe 200 and the like easily and reliably.

Chemical liquid injector 100 of the embodiment compares the check conditions stored as data with the various types of data wirelessly received from RFID chip 230, and as required, outputs the check alarm. For example, when the operator attempts to use liquid syringe 200 which is not allowed in chemical liquid injector 100 or liquid syringe 200 with the expiration date elapsed, the check alarm can be output to prevent any medical malpractice reliably.

Particularly, in chemical liquid injector 100 of the embodiment, when the data is read from RFID chip 230 of liquid syringe 200, the production number of each item is stored. If the production number newly received wirelessly from RFID chip 230 is already stored, the check alarm is output. It is thus possible to readily and reliably prevent medical malpractice such as repeated use of liquid syringe 200 which should be discarded after it is used once.

In chemical liquid injection system 1000 of the embodiment, if the variable pattern for changing the injection rate of the constant medium with time is recorded on RFID chip 230 of liquid syringe 200 of the pre-filled type filled with the contrast medium, chemical liquid injector 100 changes the injection rate of the contrast medium with time in accordance with the variable pattern.

Consequently, the optimal image contrast can be maintained favorably, and the minimum amount of the injected contrast medium can be used to reduce physical burdens on the patient. In addition, it is not necessary to previously register the data of the complicated variable pattern in chemical liquid injector 100. For example, a new variable pattern for a new contrast medium can be simply input as data to chemical liquid injector 100 from RFID chip 230 of liquid syringe 200.

In chemical liquid injector 100 of the embodiment, the pressure of the injected liquid is detected from the stress applied to piston member 220 of liquid syringe 200, and if the injection pressure reaches an abnormal value, the check alarm is output and the injection operation is forcedly stopped. This can prevent medical malpractice of injection of the liquid at an abnormal pressure.

The detection of the pressure of the liquid by chemical liquid injector 100 as described above requires not only the stress applied to piston member 220 of liquid syringe 200 but also the various types of data such as the inner diameter of cylinder member 210 and the viscosity of the liquid. The various types of data are input to chemical liquid injector 100 from RFID chip 230. Thus, in chemical liquid injection system 1000 of the embodiment, chemical liquid injector 100 can appropriately detect the injection pressure of each liquid in liquid syringe 200 without requiring complicated operations of manual entry of the various types of data into chemical liquid injector 100 by the operator.

In chemical liquid injection system 1000 of the embodiment, since the liquid injection of chemical liquid injector 100 is automatically associated with the imaging in CT scanner 300, the diagnostic images can be taken in an appropriate timing from the patient injected with the contrast medium in an appropriate timing.

Modifications of the Embodiment

The present invention is not in any way limited to the above-mentioned embodiment, but various changes and modifications may be made therein without departing from the scope of the invention. For example, in the above embodiment, a product for wireless communication with microwaves at "2.45 (GHz)" is intended as RFID chip 230. Alternatively, a product for wireless communication with UHF waves at "900 (MHz)" may be used as RFID chip 230 (not shown).

Such an RFID chip and a reader antenna thereof may be formed in a predetermined plane shape such as a square and a circle rather than an elongated shape. In this case, the orientation of the liquid syringe is detected by determining whether or not the plane directions of the chip antenna and reader antenna are substantially in parallel with each other, not the longitudinal directions.

In the above embodiment, liquid syringe 200B of the maximum size is directly mounted on chemical liquid injector 100 and liquid syringe 200S of the size other than the maximum size is mounted with cylinder adapter 400. RFID chip 230 of appropriately held liquid syringe 200B of the maximum size is located at top or bottom, and RFID chip 230 of appropriately held liquid syringe 200S of the size other than the maximum size is located on the left or right. Reader antenna 131 and resonance antennas 133 are placed at the rear of metallic flange holding mechanism 120 and auxiliary antenna 132 is disposed in front of metallic flange holding mechanism 120.

Alternatively, it is possible to provide a chemical liquid injection system (not shown) in which all of liquid syringes of various sizes are mounted on a chemical liquid injector by using cylinder adapters. In this case, the RFID chips of all of the liquid syringes can be located at the rear of metallic flange holding mechanism 120.

In this case, auxiliary antenna 132 and interfering conductor 420 of cylinder adapter 400 can be eliminated (not shown) in front of flange holding mechanism 120. The simpler structure can be used to achieve wireless communication between RFID chip 230 located on the side at the rear of flange holding mechanism 120 and RFID reader 130 through resonance antennas 133.

In such a chemical liquid injector, one of resonance antennas 133 on the left and right can be replaced with reader antenna 131 (not shown), in which case RFID chip 230 can wirelessly communicate with RFID reader 130 reliably with the simpler structure.

In the above embodiment, body portion 134 and inclined portion 135 of resonance antenna 133 are connected to each other at their lower ends. For example, body portion 134 and inclined portion 135 may be connected to each other at their upper ends or may be separated from each other (not shown.).

In the above embodiment, paired resonance antennas 133 on the left and right are spaced from each other by the distance substantially corresponding to the half wavelength in the wireless communication between RFID reader/chip 130, 230. For example, paired resonance antennas 133 on the left and right may be spaced from each other by the distance substantially corresponding to an integral multiple of the wavelength for RFID reader/chip 130, 230 (not shown).

Figure 19:
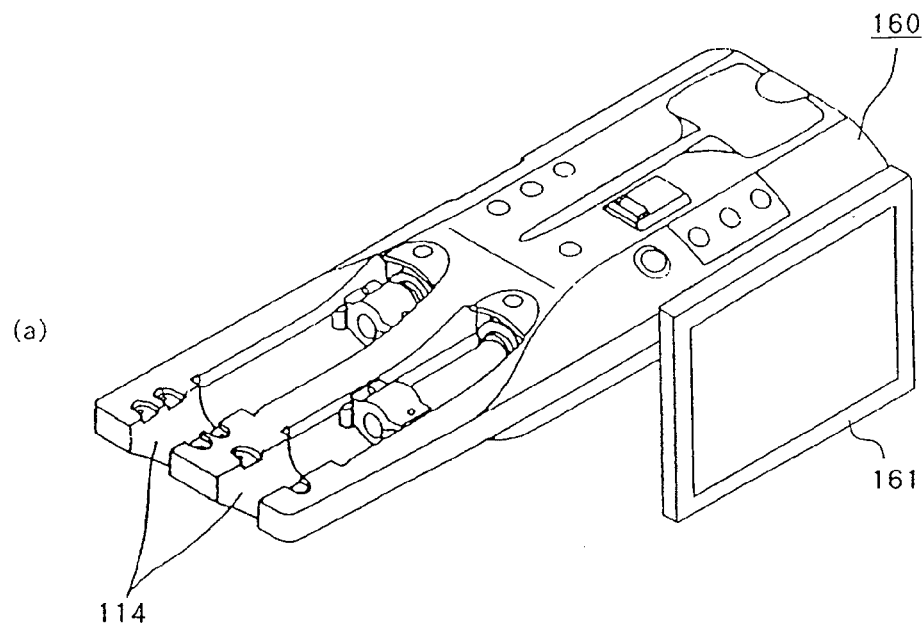
FIG. 19 is a perspective view showing the outer appearance of an injection execution head of a variation.
Figure 19:
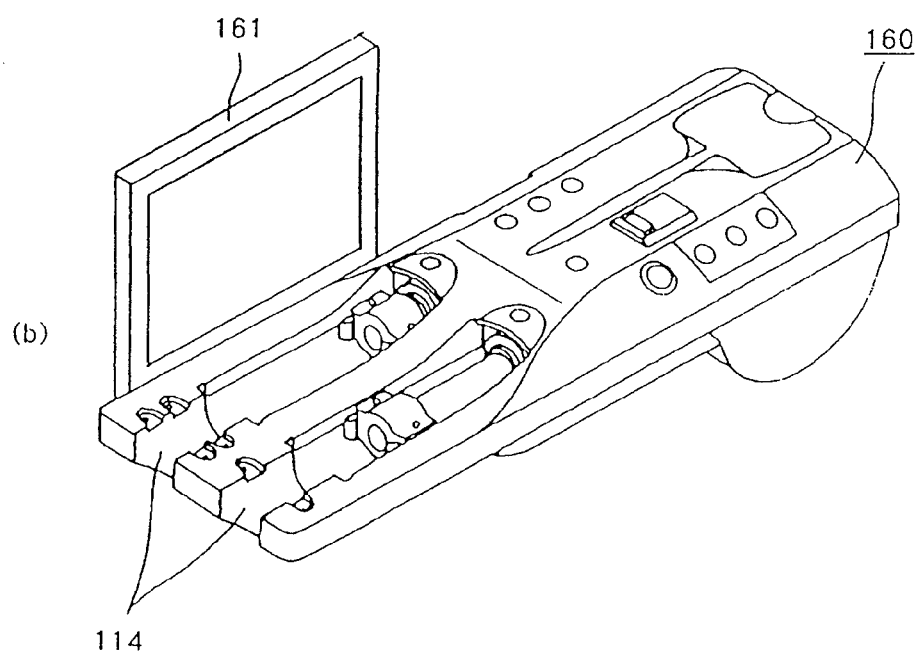

The above embodiment has shown chemical liquid injector 100 in which only one liquid syringe 200 is mounted in one concave portion 114 of injection execution head 110. As shown in FIG. 19, it is possible to provide a chemical liquid injector (not shown) in which a plurality of liquid syringes 200 are mounted individually in a plurality of concave portions 114 of injection execution head 160.

In this case, RFID reader 130 may be placed for each of concave portions 114 of injection execution head 160 to detect recorded data from each of RFID chips 230 of liquid syringes 200. Since RFID reader 130 can detect data on a plurality of RFID chips 230 in a time-division manner, RFID reader 130 may include one communication circuit and a plurality of reader antennas 131 placed for a plurality of concave portions 114.

In the above embodiment, the recorded data detected by RFID reader 130 from RFID chip 230 is output with display on liquid crystal display 104 of injection control unit 101 formed as the separate component from injection execution head 110. As shown in FIG. 19, injection execution head 160 may be provided with display panel 161 on which recorded data on RFID chip 230 may be displayed.

In this case, immediately after liquid syringe 200 is appropriately mounted in injection execution head 160, recorded data is output with display on display panel 161 of injection execution head 160. This allows immediate check of appropriate mounting of liquid syringe 200 and intuitive recognition of the displayed data.

In the above embodiment, in order to restrict the use of liquid syringe 200 and the like to once, the production number of each liquid syringe 200 is wirelessly received by RFID reader 130 from RFID chip 230 of liquid syringe 200 to be used, and is stored in chemical liquid injection 100, and if a newly wirelessly received product number is already stored, the check alarm is output.

Alternatively, it is possible that RFID chip 230 of liquid syringe 200 is a recordable product, chemical liquid injector 100 records the "used" or the fact that liquid syringe 200 has been mounted and the liquid thereof has been injected on RFID chip 230 of liquid syringe 200, and a check alarm is output when the data "used" is wirelessly received from RFID chip 230 of newly mounted liquid syringe 200.

Since a large number of production numbers do not need to be stored in chemical liquid injector 100 in this case, an overflow or the like of RAM 143 can be prevented, and RAM 143 having a large capacity does not need to be included uselessly. In addition, even when the data stored in chemical liquid injector 100 is reset erroneously, inappropriately repeated use of liquid syringe 200 or the like can be prevented.

In the above embodiment, the control data for the liquid injection is wirelessly received from RFID chip 230 of liquid syringe 200 and the like into chemical liquid injector 100, and chemical liquid injector 100 controls the operation of the liquid injection based on the control data. It is also possible that the operation of the liquid injection is controlled based on a combination of control data wirelessly received from RFID chip 230 of liquid syringe 200 and control data entered through operation panel 103 or the like.

For example, it is possible that the variable pattern of liquid injection over time is recorded on RFID chip 230 of liquid syringe 200 as described above, and when an operator enters the data of an area to be imaged by CT scanner 300 through operation panel 103 or the like, the variable pattern is adjusted in accordance with the area to be imaged.

In the above embodiment, chemical liquid injector 100 finishes the injection operation and registers the production number wirelessly received from RFID chip 230 of liquid syringe 200, and then ends the various operations. Alternatively, for example, it is possible that when chemical liquid injector 100 finishes the injection operation and registration of the production number as described above and detects removal of liquid syringe 200 with RFID reader 130, chemical liquid injector 100 automatically moves piston driving mechanism 116 backward to the initial position at the back-end.

It is also possible that when chemical liquid injector 100 completes the various operations and moves piston driving mechanism 116 back to the initial position and then detects the mounting of new liquid syringe 200 with RFID reader 130, chemical liquid injector 100 automatically moves piston driving mechanism 116 forward to the standby position for holding piston members 210. In this case, liquid syringe 200 can be removed and put in chemical liquid injector 100 in an appropriate timing to place piston driving mechanism 116 automatically to the appropriate position, so that any special operation is not required to place piston driving mechanism 116 and the convenience can be improved.

In the above embodiment, the various data are recorded by the manufacturer on RFID chip 230 of liquid syringe 200. Alternatively, the various data may be recorded on RFID chip 230 of liquid syringe 200 or the like in a medical facility such as a hospital where liquid syringe 200 is used.

In this case, desired data can be provided for liquid syringe 200 in the medial facility, and for example when a desired liquid is filled into liquid syringe 200 of the refill type, various data of the liquid can be recorded on RFID chip 230. In such a case, however, it is preferable that the production number is previously recorded inflexibly on RFID chip 230 to prevent repeated use of liquid syringe 200 as described above.

In the above embodiment, CT scanner 300 is used as the diagnostic imaging apparatus and chemical liquid injector 100 injects the contrast medium for CT. For example, an MRI apparatus or a PET apparatus may be used as the diagnostic imaging apparatus and the chemical liquid injector may inject a contrast medium therefor.

In the above embodiment, the respective portions of chemical liquid injector 100 have been specifically described, but the portions may be changed in various manners. For example, the driving source of the piston driving mechanism may be realized by a DC (Direct Current) motor or an AC (Alternating Current) motor, or the display panel may be realized by an organic EL (Electro-Luminescence) display or a plasma display (not shown).

In the above embodiment, CPU 141 operates in accordance with the computer program stored in RAM 143 or the like to realize logically various means as various functions of chemical liquid injector 100. Each of the various means may be formed as specific hardware, or some of them may be stored as software on ROM 143 or the like, while others may be formed as hardware.

The invention claimed is:

1. A chemical liquid injection system comprising at least:
a liquid syringe wherein a piston member is slidably inserted into a cylindrical member of a cylindrical shape having an annular cylinder flange formed on an outer circumference of a trailing end from the back thereof, and
a chemical liquid injector for injecting a liquid into a patient by relatively moving the cylinder member and the piston member of the liquid syringe mounted interchangeably,
wherein the liquid syringe includes an RFID chip put on an outer circumference surface of the cylinder member, the RFID chip including a chip antenna in a predetermined plane shape connected to a circuit chip to wirelessly transmit recorded data,
the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a pair of resonance antennas in a predetermined plane shape, an interfering conductor in a predetermined plane shape longer and larger than the reader antenna, and operation control means for allowing operation of the piston driving mechanism only when the recorded data is wirelessly received,
the RFID chip, in the liquid syringe, is disposed such that substantially the center of the RFID chip is located on the left or right of the cylinder member when the liquid syringe is held by the cylinder holding mechanism in a particular orientation in rotation about the axis, and
the reader antenna, in the chemical liquid injector, is disposed in a plane direction substantially in parallel with the chip antenna and below the piston member in the state in which the cylinder member is held by the cylinder holding mechanism in an orientation rotated by a right angle from the particular orientation, the paired resonance antennas is disposed in a plane direction substantially in parallel with the chip antenna and to the left and right of the piston member in the state in which the cylinder member is held by the cylinder holding mechanism in the particular orientation, and the interfering conductor is disposed in a plane direction substantially in parallel with the chip antenna and immediately below the RFID chip in the state in which the cylinder member is held by the cylinder holding mechanism in an orientation rotated by a right angle from the particular orientation.

2. A chemical liquid injection system comprising at least:
liquid syringes of various sizes, each of the syringes include a piston member slidably inserted into a cylinder member of a cylindrical shape having an annular cylinder flange formed on an outer circumference of a trailing end from the back thereof,
a cylinder adapter of at least one type provided for each of the liquid syringes of sizes other than a maximum size, and
a chemical liquid injector for injecting a liquid into a patient by relatively moving the cylinder member and the piston member of the liquid syringe of the maximum size mounted directly and the liquid syringe of a size other than the maximum size mounted with the cylinder adapter intervening between the chemical liquid injector and the liquid syringe,
wherein the liquid syringe includes an RFID chip put on an outer circumference surface of the cylinder member, the RFID chip including a chip antenna in a predetermined plane shape connected to a circuit chip to wirelessly transmit recorded data,
the chemical liquid injector includes a cylinder holding mechanism for individually holding a left portion and a right portion of the cylinder flange of the liquid syringe of the maximum size inserted from above with a pair of metallic flange holding members and for holding the cylinder adapter inserted from above, a piston driving mechanism for at least pressing the piston member into the cylinder member of the held liquid syringe, an RFID reader including a reader antenna in a predetermined plane shape connected to a communication circuit to wirelessly receive the recorded data from the RFID chip, a pair of resonance antennas in a predetermined plane shape, an auxiliary antenna in a predetermined plane shape shorter and smaller than the reader antenna, and operation control means for allowing operation of the piston driving mechanism only when the recorded data is wirelessly received,
the RFID chip, in the liquid syringe of the maximum size, is disposed such that substantially the center of the RFID chip is located at the top or bottom of the cylinder member when that liquid syringe is held by the cylinder holding mechanism in a particular orientation in rotation about the axis,
the RFID chip, in the liquid syringe of a size other than the maximum size, is disposed such that substantially the center of the RFID chip is located on the left or right of the cylinder member when that liquid syringe is held by the cylinder adapter in the cylinder holding mechanism in the particular orientation, the reader antenna is disposed in a plane direction substantially in parallel with the chip antenna and below the piston member in the state in which the liquid syringe of the maximum size is held by the cylinder holding mechanism in the particular orientation, the paired resonance antennas are disposed in a plane direction substantially in parallel with the chip antenna and to the left and right of the piston member in the state in which the liquid syringe of the maximum size is held by the cylinder holding mechanism in an orientation rotated by a right angle from the particular orientation, and the auxiliary antenna is disposed in a plane direction substantially in parallel with the chip antenna and immediately below the RFID chip in the state in which the liquid syringe of the maximum size is held by the cylinder holding mechanism in the particular orientation, in the chemical liquid injector, the cylinder adapter is formed of a material which does not prevent the wireless communication, holds at least a left portion and a right portion of the cylinder flange of the liquid syringe inserted from above, and includes an interfering conductor longer and larger than the reader antenna at a position overlapping the auxiliary antenna in the state in which the cylinder adapter is held by the cylinder holding mechanism, and the chip antenna is located at the rear of the flange holding members in the state in which the liquid syringe of a size other than the maximum size is held by the cylinder adapter put in the cylinder holding mechanism.

3. A chemical liquid injection system comprising at least:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a pair of resonance antennas in a predetermined elongated shape, an interfering conductor longer and larger than the reader antenna, and operation control means for allowing operation of the piston driving mechanism only when the recorded data is wirelessly received, RFID chip, in the liquid syringe, is disposed such that substantially the center of the RFID chip is located on the left or right of the cylinder member in the state in which the liquid syringe is held by the cylinder holding mechanism in a particular orientation in rotation about the axis, and the reader antenna is disposed in a longitudinal direction substantially in parallel with the chip antenna and below the piston member in the state in which the cylinder member is held by the cylinder holding mechanism in an orientation rotated by a right angle from the particular orientation, the paired resonance antennas are disposed in a longitudinal direction substantially in parallel with the chip antenna and en to the left and right of the piston member in the state in which the cylinder member is held by the cylinder holding mechanism in the particular orientation, and the interfering conductor is disposed in a longitudinal direction substantially in parallel with the chip antenna and immediately below the RFID chip in the state in which the cylinder member is held by the cylinder holding mechanism in an orientation rotated by a right angle from the particular orientation, the chemical liquid injector.

4. A chemical liquid injection system comprising at least:

liquid syringes of various sizes, each of the syringes include a piston member slidably inserted into a cylinder member of a cylindrical shape having an annular cylinder flange formed on an outer circumference of a trailing end from the back thereof, a cylinder adapter of at least one type provided for each of the liquid syringes of sizes other than a maximum size, and a chemical liquid injector for injecting a liquid into a patient by relatively moving the cylinder member and the piston member of the liquid syringe of the maximum size mounted directly and the liquid syringe of a size other than the maximum size mounted with the cylinder adapter intervening between the chemical liquid injector and the liquid syringe, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe of the maximum size inserted from above with a pair of metallic flange holding members and for holding the cylinder adapter inserted from above, a piston driving mechanism for at least pressing the piston member into the cylinder member of the held liquid syringe, an RFID reader including a reader antenna in a predetermined elongated shape connected to a communication circuit to wirelessly receive the recorded data from the RFID chip, a pair of resonance antennas in a predetermined elongated shape, an auxiliary antenna in a predetermined elongated shape shorter and smaller than the reader antenna, and operation control means for allowing operation of the piston driving mechanism only when the recorded data is wirelessly received, the RFID chip, in the liquid syringe of the maximum size, is disposed such that substantially the center of the RFID chip is located at the top or bottom of the cylinder member when that liquid syringe is held by the cylinder holding mechanism in a particular orientation in rotation about the axis, the RFID chip, in the liquid syringe of a size other than the maximum size, is disposed such that substantially the center of the RFID chip is located on the left or right of the cylinder member when that liquid syringe is held by the cylinder adapter in the cylinder holding mechanism in the particular orientation, the reader antenna is disposed in a longitudinal direction substantially in parallel with the chip antenna and below the piston member in the state in which the liquid syringe of the maximum size is held by the cylinder holding mechanism in the particular orientation, the paired resonance antennas are disposed in a longitudinal direction substantially in parallel with the chip antenna and to the left and right of the piston member in the state in which the liquid syringe of the maximum size is held by the cylinder holding mechanism in an orientation rotated by a right angle from the particular orientation, and the auxiliary antenna is disposed in a longitudinal direction substantially in parallel with the chip antenna and immediately below the RFID chip in the state in which the liquid syringe of the maximum size is held by the cylinder holding mechanism in the particular orientation, in the chemical liquid injector, the cylinder adapter is formed of a material which does not prevent the wireless communication, holds at least a left portion and a right portion of the cylinder flange of the liquid syringe inserted from above, and includes an interfering conductor longer and larger than the reader antenna at a position overlapping the auxiliary antenna in the state in which the cylinder adapter is held by the cylinder holding mechanism, and the chip antenna is located at the rear of the flange holding members in the state in which the liquid syringe of a size other than the maximum size is held by the cylinder adapter put in the cylinder holding mechanism.

5. The chemical liquid injection system according to claim 3, wherein the resonance antenna comprises a body portion in a predetermined elongated shape with its longitudinal direction substantially in parallel with the chip antenna in the state in which the liquid syringe of a size other than the maximum size is held by the cylinder holding mechanism in the particular orientation, and an inclined portion in a predetermined elongated shape inclined such that its upper end is located at the rear of its lower end.

6. The chemical liquid injection system according to claim 1, wherein the paired resonance antennas are spaced from each other by a distance of substantially one-half wavelength in the wireless communication.

7. The chemical liquid injection system according to claim 1, wherein the paired resonance antennas are spaced from each other by a distance of substantially an integral multiple of a wavelength in the wireless communication.

8. The chemical liquid injection system according to claim 6, wherein the RFID chip wirelessly communicates with the RFID reader at a frequency of "2.45 (GHz)", and the paired resonance antennas are spaced from each other by a distance of approximately "60 (mm)".

9. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a plane direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the reader antenna is spaced from the resonance antenna by a distance of substantially one-half wavelength in the wireless communication.

10. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a plane direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the reader antenna is spaced from the resonance antenna by a distance of substantially an integral multiple of a wavelength in the wireless communication.

11. The chemical liquid injection system according to claim 9, wherein the RFID chip wirelessly communicates with the RFID reader at a frequency of "2.45 (GHz)", and the reader antenna is spaced from the resonance antenna by a distance of approximately "60 (mm)".

12. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a plane direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein a leading end portion of the piston member is located at a trailing end portion of the cylinder member in the liquid syringe, and the RFID chip is put on the outer circumference surface of the trailing end portion of the cylinder member at a position overlapping the leading end portion of the piston member.

13. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a plane direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the RFID chip has various types of data recorded thereon as the recorded data, and the chemical liquid injector comprises data display means for outputting as display at least some of the various types of data wirelessly received from the RFID chip.

14. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a plane direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the operation control means returns the piston driving mechanism to an initial position when completion of injection operation is detected and then detection of the RFID chip by the RFID reader is ended.

15. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a plane direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the operation control means comprises data holding means for holding the various types of data wirelessly received from the RFID chip and injection control means for controlling operation of the piston driving mechanism in accordance with at least some of the various types of held data.

16. The chemical liquid injection system according to claim 15, wherein the liquid syringe is of a pre-filled type which is shipped with the liquid syringe filled with a contrast medium as the liquid to be injected into a patient whose diagnostic image is taken by a diagnostic imaging apparatus, the RFID chip of the liquid syringe having a variable pattern set thereon with which an injection rate of the contrast medium is changed with time, and the operation control means changes an operation rate of the piston driving mechanism in accordance with the variable pattern.

17. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a plane direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the operation control means comprises check storing means for storing a predetermined check condition as data, data comparing means for comparing the check condition stored as data with the various types of data wirelessly received from the RFID chip, and alarm outputting means for outputting and notifying a check alarm in accordance with the comparison result.

18. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a plane direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the RFID chip has at least a production number of the liquid syringe for each item set thereon, and the operation control means includes data accumulating means for storing data of the production number of the liquid syringe mounted and used to perform injection operation, data comparing means for comparing the stored production number with the new production number, and alarm outputting means for outputting and notifying a check alarm when the compared production numbers match.

19. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID (Radio Frequency Identification) chip put on an outer circumference surface of the cylinder member, the RFID chip including a circuit chip connected to a chip antenna in a predetermined plane shape to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from the RFID chip, a resonance antenna in a predetermined plane shape, and operation control means for allowing operation of the piston driving mechanism only when the recorded data is wirelessly received, the reader antenna is disposed in a plane direction substantially in parallel with the chip antenna and to one of the left and right of the piston member on the chemical liquid injector and the resonance antenna is disposed to the other of the left and right in the state in which the cylinder member is held b the cylinder holding mechanism in the particular orientation, in the chemical liquid injector, and wherein the RFID chip is put on the liquid syringe to record at least the fact that that liquid syringe is once used, and the operation control means includes data recording means for recording, on the RFID chip of the liquid syringe, data of the fact that that liquid syringe has been mounted and the liquid thereof has been injected, and alarm outputting means for outputting and notifying a check alarm when that data is wirelessly received from the RFID chip of the liquid syringe.

20. A chemical liquid injector for injecting a liquid into a patient by relatively moving a cylinder member and a piston member of a liquid syringe mounted interchangeably, comprising:

a cylinder holding mechanism for individually holding the left portion and the right portion of a cylinder flange formed on an outer circumference of a trailing end of a cylinder member of a liquid syringe inserted from above, a piston driving mechanism for at least pressing a piston member of the liquid syringe into the held cylinder member, an RFID reader including a reader antenna in a predetermined plane shape connected to a communication circuit to wirelessly receive recorded data from an RFID chip put on an outer circumference surface of the cylinder member, the RFID chip including a chip antenna in a predetermined plane shape connected to a circuit chip to wirelessly transmit recorded data, a pair of resonance antennas in a predetermined plane shape, an interfering conductor in a predetermined plane shape longer and larger than the reader antenna, and operation control means for allowing operation of the piston driving mechanism only when the recorded data is wirelessly received, wherein the reader antenna is disposed in a plane direction substantially in parallel with the chip antenna and below the piston member in the state in which the cylinder member is held by the cylinder holding mechanism in an orientation rotated by a right angle from the particular orientation, the paired resonance antennas are disposed in a plane direction substantially in parallel with the chip antenna and to the left and right of the piston member in the state in which the cylinder member is held by the cylinder holding mechanism in the particular orientation, and the interfering conductor is disposed in a plane direction substantially in parallel with the chip antenna and immediately below the RFID chip in the state in which the cylinder member is held by the cylinder holding mechanism in an orientation rotated by a right angle from the particular orientation.

21. A chemical liquid injector for injecting a liquid into a patient by relatively moving a cylinder member and a piston member of a liquid syringe mounted interchangeably, comprising:

a cylinder holding mechanism for individually holding the left portion and the right portion of a cylinder flange formed on an outer circumference of a trailing end of a cylinder member of a liquid syringe of the maximum size inserted from above with a pair of metallic flange holding members and for holding at least one type of cylinder adapter inserted from above, the cylinder adaptor is provided for each of liquid syringes of sizes other than the maximum size, a piston driving mechanism for at least pressing the a piston member of the liquid syringe into the held cylinder member of the liquid syringe, an RFID reader including a reader antenna in a predetermined plane shape connected to a communication circuit to wirelessly receive recorded data from an RFID chip put on an outer circumference surface of the cylinder member, the RFID chip including a chip antenna in a predetermined plane shape connected to a circuit chip to wirelessly transmit recorded data, a pair of resonance antennas in a predetermined plane shape, an auxiliary antenna in a predetermined plane shape shorter and smaller than the reader antenna, and operation control means for allowing operation of the piston driving mechanism only when the recorded data is wirelessly received, wherein the reader antenna is disposed in a plane direction substantially in parallel with the chip antenna and below the piston member in the state in which the liquid syringe of the maximum size is held by the cylinder holding mechanism in the particular orientation, the paired resonance antennas are disposed in a plane direction substantially in parallel with the chip antenna and to the left and right of the piston member in the state in which the liquid syringe of the maximum size is held by the cylinder holding mechanism in an orientation rotated by a right angle from the particular orientation, and the auxiliary antenna is disposed in a plane direction substantially in parallel with the chip antenna and immediately below the RFID chip in the state in which the liquid syringe of the maximum size is held by the cylinder holding mechanism in the particular orientation, and the chip antenna is located at the rear of the flange holding members in the state in which the liquid syringe of a size other than the maximum size is held by the cylinder adapter put in the cylinder holding mechanism.

22. A chemical liquid injector for injecting a liquid into a patient by relatively moving a cylinder member and a piston member of a liquid syringe mounted interchangeably, comprising:

a cylinder holding mechanism for individually holding the left portion and the right portion of a cylinder flange formed on an outer circumference of a trailing end of a cylinder member of a liquid syringe inserted from above, a piston driving mechanism for at least pressing a piston member of the liquid syringe into the held cylinder member, an RFID reader including a reader antenna in a predetermined elongated shape connected to a communication circuit to wirelessly receive recorded data from an RFID chip put on an outer circumference surface of the cylinder member, the RFID chip including a chip antenna in a predetermined plane shape connected to a circuit chip to wirelessly transmit recorded data, a pair of resonance antennas in a predetermined elongated shape, an interfering conductor longer and larger than the reader antenna, and operation control means for allowing operation of the piston driving mechanism only when the recorded data is wirelessly received, wherein the reader antenna is disposed in a longitudinal direction substantially in parallel with the chip antenna and below the piston member in the state in which the cylinder member is held by the cylinder holding mechanism in an orientation rotated by a right angle from the particular orientation, the paired resonance antennas are disposed in a longitudinal direction substantially in parallel with the chip antenna and to the left and right of the piston member in the state in which the cylinder member is held by the cylinder holding mechanism in the particular orientation, and the interfering conductor is disposed in a longitudinal direction substantially in parallel with the chip antenna and immediately below the RFID chip in the state in which the cylinder member is held by the cylinder holding mechanism in an orientation rotated by a right angle from the particular orientation.

23. A chemical liquid injector for injecting a liquid into a patient by relatively moving a cylinder member and a piston member of a liquid syringe mounted interchangeably, comprising:

a cylinder holding mechanism for individually holding the left portion and the right portion of a cylinder flange formed on an outer circumference of a trailing end of a cylinder member of a liquid syringe of the maximum size inserted from above with a pair of metallic flange holding members and for holding at least one type of cylinder adapter inserted from above, the cylinder adaptor is provided for each of liquid syringes of sizes other than the maximum size, a piston driving mechanism for at least pressing a piston member of the liquid syringe into the held cylinder member of the liquid syringe, an RFID reader including a reader antenna in a predetermined elongated shape connected to a communication circuit to wirelessly receive recorded data from the an RFID chip put on an outer circumference surface of the cylinder member, the RFID chip including a chip antenna in a predetermined plane shape connected to a circuit chip to wirelessly transmit recorded data, a pair of resonance antennas in a predetermined elongated shape, an auxiliary antenna in a predetermined elongated shape shorter and smaller than the reader antenna, and operation control means for allowing operation of the piston driving mechanism only when the recorded data is wirelessly received, wherein the reader antenna is disposed in a longitudinal direction substantially in parallel with the chip antenna and below the piston member in the state in which the liquid syringe of the maximum size is held by the cylinder holding mechanism in the particular orientation, the paired resonance antennas are disposed in a longitudinal direction substantially in parallel with the chip antenna and to the left and right of the piston member in the state in which the liquid syringe of the maximum size is held by the cylinder holding mechanism in an orientation rotated by a right angle from the particular orientation, and the auxiliary antenna is disposed in a longitudinal direction substantially in parallel with the chip antenna and immediately below the RFID chip in the state in which the liquid syringe of the maximum size is held by the cylinder holding mechanism in the particular orientation, and the chip antenna is located at the rear of the flange holding members in the state in which the liquid syringe of a size other than the maximum size is held by the cylinder adapter put in the cylinder holding mechanism.

24. A liquid syringe of a chemical liquid injection system the chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined plane shape connected to a communication circuit to wirelessly receive the recorded data from an RFID chip including a circuit chip connected to a chip antenna in a predetermined plane shape, a resonance antenna in a predetermined plane shape, and operation control means for allowing operation of the piston driving mechanism only when the recorded data is wirelessly received, and the reader antenna is disposed in a plane direction substantially in parallel with the chip antenna and to one of the left and right of the piston member and the resonance antenna is disposed on the other of the left and right in the state in which the cylinder member is held by the cylinder holding mechanism in the particular orientation, in the chemical liquid injector, wherein the liquid syringe includes the RFID chip put on an outer circumference surface of the cylinder member, and wherein the RFID chip is put on the liquid syringe disposed such that substantially the center of the RFID chip is located on the left or right of the outer circumference of the cylinder member when the liquid syringe is held by the cylinder holding mechanism in a particular orientation in rotation about the axis.

25. A liquid syringe of various sizes in the chemical liquid injection system according to claim 2, wherein the RFID chip is put on the liquid syringe of the maximum size disposed such that substantially the center of the RFID chip is located at the top or bottom of the outer circumference of the cylinder member when the liquid syringe of the maximum size is held by the cylinder holding mechanism in a particular orientation in rotation about the axis, and the RFID chip is put on the liquid syringe of a size other than the maximum size disposed such that substantially the center of the RFID chip is located on the left or right of the outer circumference of the cylinder member when the liquid syringe of the size other than maximum size is held by the cylinder adapter in the cylinder holding mechanism in the particular orientation.

26. A cylinder adapter in the chemical liquid injection system according to claim 2, wherein the cylinder adapter is formed of a material which does not prevent the wireless communication, individually holds the left portion and the right portion of the cylinder flange of the liquid syringe inserted from above, and includes an interfering conductor longer and larger than the reader antenna at a position overlapping the auxiliary antenna when the cylinder adapter is held by the cylinder holding mechanism.

27. The chemical liquid injection system according to claim 4, wherein the resonance antenna comprises a body portion in a predetermined elongated shape with its longitudinal direction substantially in parallel with the chip antenna in the state in which the liquid syringe of a size other than the maximum size is held by the cylinder holding mechanism in the particular orientation, and an inclined portion in a predetermined elongated shape inclined such that its upper end is located at the rear of its lower end.

28. The chemical liquid injection system according to claim 2, wherein the paired resonance antennas are spaced from each other by a distance of substantially one-half wavelength in the wireless communication.

29. The chemical liquid injection system according to claim 28, wherein the RFID chip wirelessly communicates with the RFID reader at a frequency of "2.45 (GHz)", and the paired resonance antennas are spaced from each other by a distance of approximately "60 (mm)".

30. The chemical liquid injection system according to claim 3, wherein the paired resonance antennas are spaced from each other by a distance of substantially one-half wavelength in the wireless communication.

31. The chemical liquid injection system according to claim 30, wherein the RFID chip wirelessly communicates with the RFID reader at a frequency of "2.45 (GHz)", and the paired resonance antennas are spaced from each other by a distance of approximately "60 (mm)".

32. The chemical liquid injection system according to claim 4, wherein the paired resonance antennas are spaced from each other by a distance of substantially one-half wavelength in the wireless communication.

33. The chemical liquid injection system according to claim 32, wherein the RFID chip wirelessly communicates with the RFID reader at a frequency of "2.45 (GHz)", and the paired resonance antennas are spaced from each other by a distance of approximately "60 (mm)".

34. The chemical liquid injection system according to claim 2, wherein the paired resonance antennas are spaced from each other by a distance of substantially an integral multiple of a wavelength in the wireless communication.

35. The chemical liquid injection system according to claim 3, wherein the paired resonance antennas are spaced from each other by a distance of substantially an integral multiple of a wavelength in the wireless communication.

36. The chemical liquid injection system according to claim 4, wherein the paired resonance antennas are spaced from each other by a distance of substantially an integral multiple of a wavelength in the wireless communication.

37. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the reader antenna is spaced from the resonance antenna by a distance of substantially one-half wavelength in the wireless communication.

38. The chemical liquid injection system according to claim 37, wherein the RFID chip wirelessly communicates with the RFID reader at a frequency of "2.45 (GHz)", and the reader antenna is spaced from the resonance antenna by a distance of approximately "60 (mm)".

39. The A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the reader antenna is spaced from the resonance antenna by a distance of substantially an integral multiple of a wavelength in the wireless communication.

40. The chemical liquid injection system according to claim 1, wherein a leading end portion of the piston member is located at a trailing end portion of the cylinder member in the liquid syringe, and the RFID chip is put on the outer circumference surface of the trailing end portion of the cylinder member at a position overlapping the leading end portion of the piston member.

41. The chemical liquid injection system according to claim 2, wherein a leading end portion of the piston member is located at a trailing end portion of the cylinder member in the liquid syringe, and the RFID chip is put on the outer circumference surface of the trailing end portion of the cylinder member at a position overlapping the leading end portion of the piston member.

42. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein a leading end portion of the piston member is located at a trailing end portion of the cylinder member in the liquid syringe, and the RFID chip is put on the outer circumference surface of the trailing end portion of the cylinder member at a position overlapping the leading end portion of the piston member.

43. The chemical liquid injection system according to claim 3, wherein a leading end portion of the piston member is located at a trailing end portion of the cylinder member in the liquid syringe, and the RFID chip is put on the outer circumference surface of the trailing end portion of the cylinder member at a position overlapping the leading end portion of the piston member.

44. The chemical liquid injection system according to claim 4, wherein a leading end portion of the piston member is located at a trailing end portion of the cylinder member in the liquid syringe, and the RFID chip is put on the outer circumference surface of the trailing end portion of the cylinder member at a position overlapping the leading end portion of the piston member.

45. The chemical liquid injection system according to claim 1, wherein the RFID chip has various types of data recorded thereon as the recorded data, and the chemical liquid injector comprises data display means for outputting as display at least some of the various types of data wirelessly received from the RFID chip.

46. The chemical liquid injection system according to claim 2, wherein the RFID chip has various types of data recorded thereon as the recorded data, and the chemical liquid injector comprises data display means for outputting as display at least some of the various types of data wirelessly received from the RFID chip.

47. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the RFID chip has various types of data recorded thereon as the recorded data, and the chemical liquid injector comprises data display means for outputting as display at least some of the various types of data wirelessly received from the RFID chip.

48. The chemical liquid injection system according to claim 3, wherein the RFID chip has various types of data recorded thereon as the recorded data, and the chemical liquid injector comprises data display means for outputting as display at least some of the various types of data wirelessly received from the RFID chip.

49. The chemical liquid injection system according to claim 4, wherein the RFID chip has various types of data recorded thereon as the recorded data, and the chemical liquid injector comprises data display means for outputting as display at least some of the various types of data wirelessly received from the RFID chip.

50. The chemical liquid injection system according to claim 1, wherein the operation control means returns the piston driving mechanism to an initial position when completion of injection operation is detected and then detection of the RFID chip by the RFID reader is ended.

51. The chemical liquid injection system according to claim 2, wherein the operation control means returns the piston driving mechanism to an initial position when completion of injection operation is detected and then detection of the RFID chip by the RFID reader is ended.

52. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the operation control means returns the piston driving mechanism to an initial position when completion of injection operation is detected and then detection of the RFID chip by the RFID reader is ended.

53. The chemical liquid injection system according to claim 3, wherein the operation control means returns the piston driving mechanism to an initial position when completion of injection operation is detected and then detection of the RFID chip by the RFID reader is ended.

54. The chemical liquid injection system according to claim 4, wherein the operation control means returns the piston driving mechanism to an initial position when completion of injection operation is detected and then detection of the RFID chip by the RFID reader is ended.

55. The chemical liquid injection system according to claim 1, wherein the operation control means comprises data holding means for holding the various types of data wirelessly received from the RFID chip and injection control means for controlling operation of the piston driving mechanism in accordance with at least some of the various types of held data.

56. The chemical liquid injection system according to claim 55, wherein the liquid syringe is of a pre-filled type which is shipped with the liquid syringe filled with a contrast medium as the liquid to be injected into a patient whose diagnostic image is taken by a diagnostic imaging apparatus, the RFID chip of the liquid syringe having a variable pattern set thereon with which an injection rate of the contrast medium is changed with time, and the operation control means changes an operation rate of the piston driving mechanism in accordance with the variable pattern.

57. The chemical liquid injection system according to claim 2, wherein the operation control means comprises data holding means for holding the various types of data wirelessly received from the RFID chip and injection control means for controlling operation of the piston driving mechanism in accordance with at least some of the various types of held data.

58. The chemical liquid injection system according to claim 57, wherein the liquid syringe is of a pre-filled type which is shipped with the liquid syringe filled with a contrast medium as the liquid to be injected into a patient whose diagnostic image is taken by a diagnostic imaging apparatus, the RFID chip of the liquid syringe having a variable pattern set thereon with which an injection rate of the contrast medium is changed with time, and the operation control means changes an operation rate of the piston driving mechanism in accordance with the variable pattern.

59. A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the operation control means comprises data holding means for holding the various types of data wirelessly received from the RFID chip and injection control means for controlling operation of the piston driving mechanism in accordance with at least some of the various types of held data.

60. The chemical liquid injection system according to claim 59, wherein the liquid syringe is of a pre-filled type which is shipped with the liquid syringe filled with a contrast medium as the liquid to be injected into a patient whose diagnostic image is taken by a diagnostic imaging apparatus, the RFID chip of the liquid syringe having a variable pattern set thereon with which an injection rate of the contrast medium is changed with time, and the operation control means changes an operation rate of the piston driving mechanism in accordance with the variable pattern.

61. The chemical liquid injection system according to claim 3, wherein the operation control means comprises data holding means for holding the various types of data wirelessly received from the RFID chip and injection control means for controlling operation of the piston driving mechanism in accordance with at least some of the various types of held data.

62. The chemical liquid injection system according to claim 61, wherein the liquid syringe is of a pre-filled type which is shipped with the liquid syringe filled with a contrast medium as the liquid to be injected into a patient whose diagnostic image is taken by a diagnostic imaging apparatus, the RFID chip of the liquid syringe having a variable pattern set thereon with which an injection rate of the contrast medium is changed with time, and the operation control means changes an operation rate of the piston driving mechanism in accordance with the variable pattern.

63. The chemical liquid injection system according to claim 4, wherein the operation control means comprises data holding means for holding the various types of data wirelessly received from the RFID chip and injection control means for controlling operation of the piston driving mechanism in accordance with at least some of the various types of held data.

64. The chemical liquid injection system according to claim 63, wherein the liquid syringe is of a pre-filled type which is shipped with the liquid syringe filled with a contrast medium as the liquid to be injected into a patient whose diagnostic image is taken by a diagnostic imaging apparatus, the RFID chip of the liquid syringe having a variable pattern set thereon with which an injection rate of the contrast medium is changed with time, and the operation control means changes an operation rate of the piston driving mechanism in accordance with the variable pattern.

65. The chemical liquid injection system according to claim 1, wherein the operation control means comprises check storing means for storing a predetermined check condition as data, data comparing means for comparing the check condition stored as data with the various types of data wirelessly received from the RFID chip, and alarm outputting means for outputting and notifying a check alarm in accordance with the comparison result.

66. The chemical liquid injection system according to claim 2, wherein the operation control means comprises check storing means for storing a predetermined check condition as data, data comparing means for comparing the check condition stored as data with the various types of data wirelessly received from the RFID chip, and alarm outputting means for outputting and notifying a check alarm in accordance with the comparison result.

67. A chemical liquid injection system comprising:
a liquid syringe wherein a piston member is slidably inserted into a cylindrical member of a cylindrical shape having an annular cylinder flange formed on an outer circumference of a trailing end from the back thereof, and
a chemical liquid injector for injecting a liquid into a patient by relatively moving the cylinder member and the piston member of the liquid syringe mounted interchangeably,
wherein the liquid syringe includes an RFID chip wound and put on an outer circumference surface of the cylinder member, the RFID chip including a chip antenna in a predetermined elongated shape connected to a circuit chip to wirelessly transmit recorded data,
the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received,
the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the operation control means comprises check storing means for storing a predetermined check condition as data, data comparing means for comparing the check condition stored as data with the various types of data wirelessly received from the RFID chip, and alarm outputting means for outputting and notifying a check alarm in accordance with the comparison result.

68. The chemical liquid injection system according to claim 3, wherein the operation control means comprises check storing means for storing a predetermined check condition as data, data comparing means for comparing the check condition stored as data with the various types of data wirelessly received from the RFID chip, and alarm outputting means for outputting and notifying a check alarm in accordance with the comparison result.

69. The chemical liquid injection system according to claim 4, wherein the operation control means comprises check storing means for storing a predetermined check condition as data, data comparing means for comparing the check condition stored as data with the various types of data wirelessly received from the RFID chip, and alarm outputting means for outputting and notifying a check alarm in accordance with the comparison result.

70. The chemical liquid injection system according to claim 1, wherein the RFID chip has at least a production number of the liquid syringe for each item set thereon, and the operation control means includes data accumulating means for storing data of the production number of the liquid syringe mounted and used to perform injection operation, data comparing means for comparing the stored production number with the new production number, and alarm outputting means for outputting and notifying a check alarm when the compared production numbers match.

71. The chemical liquid injection system according to claim 2, wherein the RFID chip has at least a production number of the liquid syringe for each item set thereon, and the operation control means includes data accumulating means for storing data of the production number of the liquid syringe mounted and used to perform injection operation, data comparing means for comparing the stored production number with the new production number, and alarm outputting means for outputting and notifying a check alarm when the compared production numbers match.

72. A chemical liquid injection system comprising:
a liquid syringe wherein a piston member is slidably inserted into a cylindrical member of a cylindrical shape having an annular cylinder flange formed on an outer circumference of a trailing end from the back thereof, and
a chemical liquid injector for injecting a liquid into a patient by relatively moving the cylinder member and the piston member of the liquid syringe mounted interchangeably,
wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the RFID chip has at least a production number of the liquid syringe for each item set thereon, and the operation control means includes data accumulating means for storing data of the production number of the liquid syringe mounted and used to perform injection operation, data comparing means for comparing the stored production number with the new production number, and alarm outputting means for outputting and notifying a check alarm when the compared production numbers match.

73. The chemical liquid injection system according to claim 3, wherein the RFID chip has at least a production number of the liquid syringe for each item set thereon, and the operation control means includes data accumulating means for storing data of the production number of the liquid syringe mounted and used to perform injection operation, data comparing means for comparing the stored production number with the new production number, and alarm outputting means for outputting and notifying a check alarm when the compared production numbers match.

74. The chemical liquid injection system according to claim 4, wherein the RFID chip has at least a production number of the liquid syringe for each item set thereon, and the operation control means includes data accumulating means for storing data of the production number of the liquid syringe mounted and used to perform injection operation, data comparing means for comparing the stored production number with the new production number, and alarm outputting means for outputting and notifying a check alarm when the compared production numbers match.

75. The chemical liquid injection system according to claim 1, wherein the RFID chip is put on the liquid syringe to record at least the fact that that liquid syringe is once used, and the operation control means includes data recording means for recording, on the RFID chip of the liquid syringe, data of the fact that that liquid syringe has been mounted and the liquid thereof has been injected, and alarm outputting means for outputting and notifying a check alarm when that data is wirelessly received from the RFID chip of the liquid syringe.

76. The chemical liquid injection system according to claim 2, wherein the RFID chip is put on the liquid syringe to record at least the fact that that liquid syringe is once used, and the operation control means includes data recording means for recording, on the RFID chip of the liquid syringe, data of the fact that that liquid syringe has been mounted and the liquid thereof has been injected, and alarm outputting means for outputting and notifying a check alarm when that data is wirelessly received from the RFID chip of the liquid syringe.

77. The A chemical liquid injection system comprising:

a liquid syringe wherein a piston member is slidably inserted into a cylindrical member of a cylindrical shape having an annular cylinder flange formed on an outer circumference of a trailing end from the back thereof, and a chemical liquid injector for injecting a liquid into a patient by relatively moving the cylinder member and the piston member of the liquid syringe mounted interchangeably, wherein the liquid syringe includes an RFID chip wound and put on an outer circumference surface of the cylinder member, the RFID chip including a chip antenna in a predetermined elongated shape connected to a circuit chip to wirelessly transmit recorded data, the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive the recorded data from the RFID chip, a resonance antenna in a predetermined elongated shape, and operation control means for allowing operation of the piston driving mechanism only when the recorded data is wirelessly received, the RFID chip, in the liquid syringe, is disposed such that substantially the center of the RFID chip is located on the left or right of the cylinder member when the liquid syringe is held by the cylinder holding mechanism in a particular orientation in rotation about the axis, and the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector, and wherein the RFID chip is put on the liquid syringe to record at least the fact that that liquid syringe is once used, and the operation control means includes data recording means for recording, on the RFID chip of the liquid syringe, data of the fact that that liquid syringe has been mounted and the liquid thereof has been injected, and alarm outputting means for outputting and notifying a check alarm when that data is wirelessly received from the RFID chip of the liquid syringe.

78. The chemical liquid injection system according to claim 3, wherein the RFID chip is put on the liquid syringe to record at least the fact that that liquid syringe is once used, and the operation control means includes data recording means for recording, on the RFID chip of the liquid syringe, data of the fact that that liquid syringe has been mounted and the liquid thereof has been injected, and alarm outputting means for outputting and notifying a check alarm when that data is wirelessly received from the RFID chip of the liquid syringe.

79. The chemical liquid injection system according to claim 4, wherein the RFID chip is put on the liquid syringe to record at least the fact that that liquid syringe is once used, and
the operation control means includes data recording means for recording, on the RFID chip of the liquid syringe, data of the fact that that liquid syringe has been mounted and the liquid thereof has been injected, and alarm outputting means for outputting and notifying a check alarm when that data is wirelessly received from the RFID chip of the liquid syringe.

80. A liquid syringe of the chemical liquid injection system according to claim 1,
wherein the RFID chip is put on the liquid syringe disposed such that substantially the center of the RFID chip is located on the left or right of the outer circumference of the cylinder member when the liquid syringe is held by the cylinder holding mechanism in a particular orientation in rotation about the axis.

81. A liquid syringe of a chemical liquid injection system, the chemical liquid injection system comprising:
a liquid syringe wherein a piston member is slidably inserted into a cylindrical member of a cylindrical shape having an annular cylinder flange formed on an outer circumference of a trailing end from the back thereof, and
a chemical liquid injector for injecting a liquid into a patient by relatively moving the cylinder member and the piston member of the liquid syringe mounted interchangeably,
the chemical liquid injector includes a cylinder holding mechanism for individually holding a left portion and a right portion of the cylinder flange of the liquid syringe inserted from above, a piston driving mechanism for at least pressing the piston member into the held cylinder member, an RFID reader including a reader antenna in a predetermined elongated shape connected to a communication circuit to wirelessly receive recorded data from an RFID chip including a circuit chip connected to a chip antenna in a predetermined plate shape, a resonance antenna in a predetermined elongated shape, and operation control means for allowing operation of the piston driving mechanism only when the recorded data is wirelessly received,
the reader antenna is disposed in a longitudinal direction substantially in parallel with the chip antenna and to one of the left and right of the piston member on the chemical liquid injector and the resonance antenna is disposed to the other of the left and right in the state in which the cylinder member is held by the cylinder holding mechanism in the particular orientation, in the chemical liquid injector,
wherein the liquid syringe includes the RFID chip put on an outer circumference surface of the cylinder member, and
wherein the RFID chip is put on the liquid syringe disposed such that substantially the center of the RFID chip is located on the left or right of the outer circumference of the cylinder member when the liquid syringe is held by the cylinder holding mechanism in a particular orientation in rotation about the axis.

82. A liquid syringe of the chemical liquid injection system according to claim 3,
wherein the RFID chip is put on the liquid syringe disposed such that substantially the center of the RFID chip is located on the left or right of the outer circumference of the cylinder member when the liquid syringe is held by the cylinder holding mechanism in a particular orientation in rotation about the axis.

83. A liquid syringe of various sizes in the chemical liquid injection system according to claim 4,
wherein the RFID chip is put on the liquid syringe of the maximum size disposed such that substantially the center of the RFID chip is located at the top or bottom of the outer circumference of the cylinder member when the liquid syringe of the maximum size is held by the cylinder holding mechanism in a particular orientation in rotation about the axis, and
the RFID chip is put on the liquid syringe of a size other than the maximum size disposed such that substantially the center of the RFID chip is located on the left or right of the outer circumference of the cylinder member when the liquid syringe of the size other than maximum size is held by the cylinder adapter in the cylinder holding mechanism in the particular orientation.

84. A cylinder adapter in the chemical liquid injection system according to claim 4,
wherein the cylinder adapter is formed of a material which does not prevent the wireless communication, individually holds the left portion and the right portion of the cylinder flange of the liquid syringe inserted from above, and includes an interfering conductor longer and larger than the reader antenna at a position overlapping the auxiliary antenna when the cylinder adapter is held by the cylinder holding mechanism.

* * * * *

UNITED STATES PATENT AND TRADEMARK OFFICE
CERTIFICATE OF CORRECTION

| | | |
|---|---|---|
| PATENT NO. | : 7,887,513 B2 | Page 1 of 1 |
| APPLICATION NO. | : 11/719089 | |
| DATED | : February 15, 2011 | |
| INVENTOR(S) | : Shigeru Nemoto et al. | |

It is certified that error appears in the above-identified patent and that said Letters Patent is hereby corrected as shown below:

Column 5, Line 33, change "RIFD" to --RFID--.

Column 6, Line 25, change "he" to --the--.

Column 7, Line 10, change "RIFD" to --RFID--.

Column 11, Line 49, change "FRID" to --RFID--.

Column 21, Line 30, change "the a" to --a--.

Column 23, Line 37, change "(not shown.)." to --(not shown).--.

Column 28, Line 8, in Claim 3, after "antenna and" delete "en".

Column 36, Line 12, in Claim 19, change "held b" to --held by--.

Column 37, Line 14, in Claim 21, after "pressing" delete "the".

Column 38, Line 44, in Claim 23, after "from" delete "the".

Column 39, Line 10, in Claim 24, change "system" to --system,--.

Column 41, Line 43, in Claim 39, before "A chemical" delete "The".

Column 50, Line 14, in Claim 77, before "A chemical" delete "The".

Signed and Sealed this
Sixth Day of March, 2012

David J. Kappos
*Director of the United States Patent and Trademark Office*